(12) United States Patent
Dolan et al.

(10) Patent No.: US 10,328,002 B2
(45) Date of Patent: Jun. 25, 2019

(54) DENTIFRICE COMPOSITIONS CONTAINING STANNOUS COMPATIBLE SILICA PARTICLES

(71) Applicant: The Procter & Gamble Company, Cincinnati, OH (US)

(72) Inventors: Lawrence Edward Dolan, Cincinnati, OH (US); Sanjeev Midha, Mason, OH (US); Eva Schneiderman, Mason, OH (US); Karl William Gallis, Perryville, MD (US); William Jackson Hagar, Perryville, MD (US); Terry William Nassivera, Gambrills, MD (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 15/829,559

(22) Filed: Dec. 1, 2017

(65) Prior Publication Data

US 2018/0168958 A1    Jun. 21, 2018

Related U.S. Application Data

(60) Provisional application No. 62/435,868, filed on Dec. 19, 2016, provisional application No. 62/509,703, filed on May 22, 2017.

(51) Int. Cl.
| | | |
|---|---|---|
| *A61K 8/25* | (2006.01) | |
| *A61Q 11/00* | (2006.01) | |
| *A61K 8/27* | (2006.01) | |
| *A61K 8/19* | (2006.01) | |
| *A61K 8/02* | (2006.01) | |

(52) U.S. Cl.
CPC ............. *A61K 8/25* (2013.01); *A61K 8/0241* (2013.01); *A61K 8/19* (2013.01); *A61K 8/27* (2013.01); *A61Q 11/00* (2013.01); *A61K 2800/28* (2013.01); *A61K 2800/60* (2013.01)

(58) Field of Classification Search
None
See application file for complete search history.

(56) References Cited

U.S. PATENT DOCUMENTS

| | | |
|---|---|---|
| 4,340,583 A | 7/1982 | Wason |
| 4,420,312 A | 12/1983 | Wason |
| 5,869,028 A * | 2/1999 | McGill ............ A61K 8/25 423/339 |
| 6,946,119 B2 | 9/2005 | Gallis et al. |
| 7,255,852 B2 | 8/2007 | Gallis et al. |
| 7,438,895 B2 | 10/2008 | Gallis |
| 8,211,406 B2 | 7/2012 | Baig et al. |
| 8,211,407 B2 | 7/2012 | Deckner et al. |
| 8,211,408 B2 | 7/2012 | Baig et al. |
| 8,211,409 B2 | 7/2012 | Baig et al. |
| 8,211,410 B2 | 7/2012 | Baig et al. |
| 8,211,411 B2 | 7/2012 | Deckner et al. |
| 8,216,552 B2 | 7/2012 | Deckner et al. |
| 8,216,553 B2 | 7/2012 | Hughes et al. |
| 8,221,722 B2 | 7/2012 | Baig et al. |
| 8,221,723 B2 | 7/2012 | Deckner et al. |
| 8,221,724 B2 | 7/2012 | Deckner et al. |
| 8,221,725 B2 | 7/2012 | Deckner et al. |
| 8,221,726 B2 | 7/2012 | Deckner et al. |
| 8,226,932 B2 | 7/2012 | Haught et al. |
| 8,293,216 B2 | 10/2012 | Deckner et al. |
| 8,551,457 B2 | 10/2013 | Deckner et al. |
| 8,795,637 B2 | 8/2014 | Deckner et al. |
| 2004/0161389 A1 | 8/2004 | Gallis et al. |
| 2004/0161390 A1 | 8/2004 | Gallis et al. |
| 2005/0032965 A1 | 2/2005 | Valero |
| 2008/0160052 A1 | 7/2008 | Gallis |
| 2010/0135921 A1 * | 6/2010 | Hughes ............ A61K 8/25 424/49 |
| 2010/0310614 A1 * | 12/2010 | Strand ............. A61K 8/20 424/401 |
| 2012/0219606 A1 * | 8/2012 | Deckner .......... A61K 8/25 424/401 |
| 2014/0127145 A1 * | 5/2014 | Deckner ........ A61K 8/0241 424/57 |

FOREIGN PATENT DOCUMENTS

| | | |
|---|---|---|
| EP | 2246031 | 11/2010 |
| WO | WO2015171836 | 11/2015 |
| WO | WO2018114280 | 6/2018 |

OTHER PUBLICATIONS

International Search Report with written opinion, dated Mar. 23, 2018, 13 pages.

\* cited by examiner

*Primary Examiner* — Isaac Shomer
(74) *Attorney, Agent, or Firm* — James E. Oehlenschlager; James J Camp

(57) ABSTRACT

A dentifrice composition containing an abrasive and a stannous ion source. The abrasive can contain precipitated silica particles where the extractable stannous ions after 30 days at 40° C. is greater than about 75% of the initial extractable stannous ion concentration.

19 Claims, 13 Drawing Sheets

DENTIFRICE COMPOSITIONS CONTAINING STANNOUS COMPATIBLE SILICA PARTICLES

BACKGROUND OF THE INVENTION

Compositions containing stannous, including stannous fluoride, are a very effective therapeutic agent used in dentifrices and other end-use applications, providing improved cavity protection and reduced plaque, gingivitis, and tooth sensitivity. However, the effectiveness of stannous in a dentifrice formulation can be diminished due to interactions with other components of the formulation, such as silica materials.

Therefore, it would be beneficial to provide a dentifrice composition containing silica materials with improved stannous compatibility to improve the overall effectiveness of the stannous. Accordingly, it is to this end that the present invention is principally directed.

SUMMARY OF THE INVENTION

A dentifrice composition comprising an abrasive comprising precipitated silica particles characterized by; a BET surface area in a range from about 0.1 to about 9 m$^2$/g; a pack density in a range from about 35 to about 55 lb/ft$^3$; an Einlehner abrasion value in a range from about 8 to about 25 mg lost/100,000 revolutions; a total mercury intrusion pore volume in a range from about 0.4-1.2 cc/g; and a stannous compatibility in a range from about 70 to about 99%; a stannous ion source wherein the extractable stannous ions after 30 days at 40° C. is greater than about 75% of the initial extractable stannous ion concentration.

A dentifrice composition comprising an abrasive comprising precipitated silica particles characterized by; a BET surface area in a range from about 0.1 to about 9 m$^2$/g; a pack density in a range from about 35 to about 55 lb/ft$^3$; an Einlehner abrasion value in a range from about 8 to about 25 mg lost/100,000 revolutions; a total mercury intrusion pore volume in a range from about 0.4-1.2 cc/g; and a stannous compatibility in a range from about 70 to about 99%; a stannous ion source wherein an extractable stannous ion concentration after 30 days at 40° C. is greater than about 75% of the initial extractable stannous ion concentration; a fluoride ion source wherein the percent soluble fluoride after 30 days at 40° C. is greater than about 75% of the initial fluoride concentration; wherein the average RDA is less than about 250.

A dentifrice composition comprising an abrasive comprising precipitated silica characterized by; a BET surface area in a range from about 0.1 to about 9 m$^2$/g; a pack density in a range from about 35 to about 55 lb/ft$^3$; an Einlehner abrasion value in a range from about 8 to about 25 mg lost/100,000 revolutions; a total mercury intrusion pore volume in a range from about 0.4-1.2 cc/g; and a stannous compatibility in a range from about 70 to about 99%; a stannous ion source wherein the composition wherein an extractable stannous ions after 30 days at 40° C. is greater than about 80% of the initial extractable stannous ion concentration; an optional soluble fluoride ion source wherein the composition comprises from about 550 ppm to about 1100 ppm soluble fluoride ions; wherein the dentifrice composition has an average RDA less than about 250; wherein the dentifrice composition has an average PCR greater than about 90.

DEFINITIONS

Figure 1:
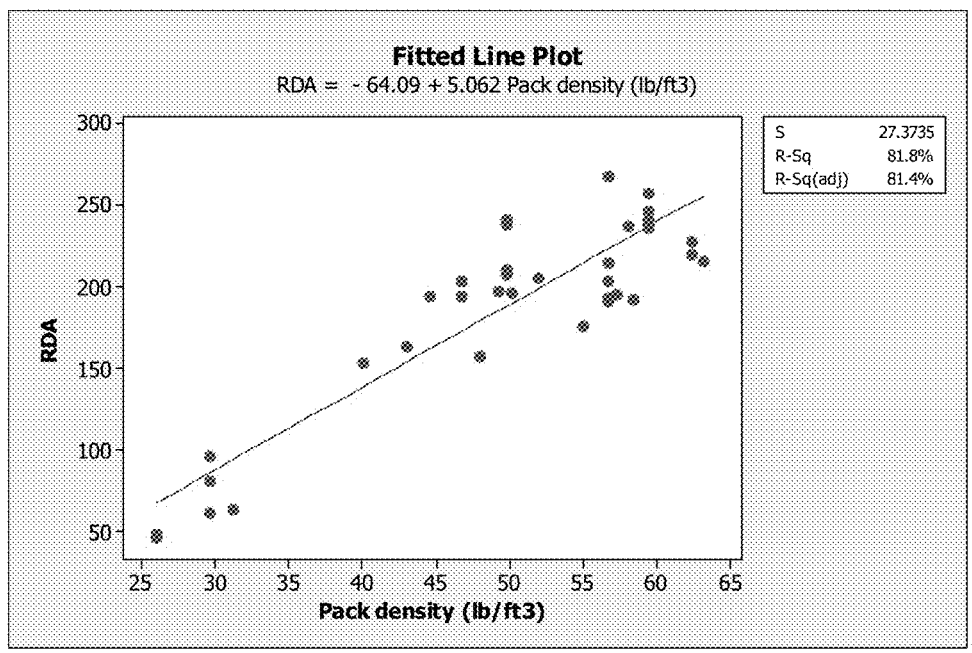
FIG. 1 is a graph showing the correlation between dentifrice Radioactive Dentine Abrasion (RDA) and pack density of surface area reduced silica particles.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise.

The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

As used herein, the word "include," and its variants, are intended to be non-limiting, such that recitation of items in a list is not to the exclusion of other like items that may also be useful in the materials, compositions, devices, and methods of this invention.

As used herein, the word "or" when used as a connector of two or more elements is meant to include the elements individually and in combination; for example X or Y, means X or Y or both.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side. As Herein, the terms "toothpaste" and "dentifrice" can be used interchangeably.

The term "water", as used herein, refers to USP water, unless otherwise specified.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the BET surface area of the silica particles can be in certain ranges in various aspects of this invention. By a disclosure that the BET surface area is in a range from about 0.1 to about 9 m$^2$/g or from about 0.1 to about 7 m$^2$/g, the intent is to recite that the surface area can be any surface area within the range and, for example, can be equal to about 0.1, about 0.2, about 0.5, about 1, about 2, about 3, about 5, about 6, about 7, or about 9 m$^2$/g. Additionally, the surface area can be within any range from about 0.1 to about 9 m$^2$/g (for example, from about 0.1 to about 5 m$^2$/g), and this also includes any combination of ranges between about 0.1 and about 9 m$^2$/g (for example, the surface area can be in a range from about 0.1 to about 2 m$^2$/g or from about 3 to about 4.5 m$^2$/g). Likewise, all other ranges disclosed herein should be interpreted in a manner similar to this example.

The term "about" means that amounts, sizes, formulations, parameters, and other quantities and characteristics are not and need not be exact, but may be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

DETAILED DESCRIPTION OF THE INVENTION

The present invention is directed towards dentifrice compositions containing silica particles with improved stannous compatibility. As an initial matter, it was found that previous metrics and characteristics of silica properties were insufficient to adequately predict stannous compatibility. For instance, CPC (cetylpyridinium chloride) compatibility with silica materials is often a known property, but CPC compatibility is not necessarily a useful measure of stannous compatibility. The CPC molecules, being much larger than stannous ions, cannot access the surface area in the silica particles that result from small pores of less than approximately 500 angstroms (Å) ("small pore(s)"), as described in U.S. Pat. No. 7,255,852, incorporated herein by reference in its entirety. In contrast, stannous ions can access substantially all of the porosity resulting from such small pores, and interact and bind to the surfaces within the small pores, thereby limiting the availability and therapeutic effectiveness of stannous ions. Accordingly, the surface area reduction of pore sizes to promote CPC compatibility is not the same as the surface area reduction of pore sizes to promote stannous compatibility.

While not wishing to be bound by the following theory, it is believed that eliminating the small pore porosity from within the silica particles is an important factor toward achieving high stannous compatibility. However, when all of the pores, regardless of size or surface area, within the particles are filled in, the resulting silica particles are very hard, too dense, and too abrasive. Unexpectedly, and beneficially, it was found that the surface area resulting from small pores can be filled in and eliminated, without eliminating the pores of greater than approximately 1000 Å ("the large pore(s)") of the silica particles, by a surface area reduction step. The resulting surface area reduced silica particles—with only the small pore porosity eliminated (from pores less than approximately 500-1000 Å)—were found to be highly compatible with stannous ions, and moreover, they maintained enough porosity resulting from the large pores such that their particle pack density and abrasivity were not dramatically increased. In general, the most effective surface area reduced silica particles had low BET surface areas (e.g., a minimized level of porosity resulting from small pores) and low particle pack densities and low abrasiveness (e.g., the required amount of porosity resulting from large pores).

Generally, small pore porosity can be characterized or quantified by the BET surface area such that low BET surface area values generally correlate to having less small pore porosity resulting in silica particles that do not absorb stannous ions thus producing high stannous compatible materials. The large pore porosity can be characterized or quantified by the total intrusion mercury volume and/or the pack density such that high pore volume values and low pack density values generally correlate to having more large pore porosity resulting in silica particles that produce dentifrice compositions with appropriate RDA values.

Figure 2:
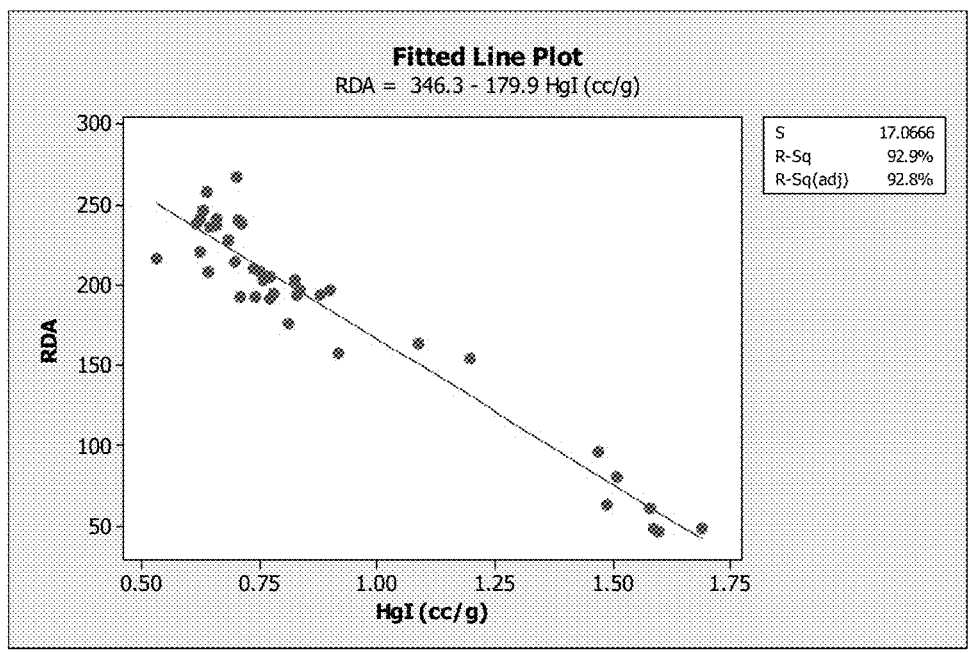
FIG. 2 is a graph showing the correlation between dentifrice RDA and total mercury intrusion pore volume of surface area reduced silica particles

RDA testing is typically performed to confirm that a dentifrice composition, i.e. toothpaste, is safe for consumer use, with the upper limit of the test set at 250. Due to the variability in this testing methodology, several independent replicates of RDA may be desired. Unexpectedly, a strong correlation exists between dentifrice RDA values and pore volume of the silica particles and between dentifrice RDA values and pack density of the silica particles as shown in FIG. 1 and FIG. 2, respectively. Since RDA testing is performed at a limited number of external testing laboratories and is expensive and time consuming, correlating physical properties of the silica particles to dentifrice RDA allowed for determination of key properties of the silica particles without solely relying on RDA. As the pack density of the silica particles is increased, the dentifrice RDA increases. Correspondingly, as the total mercury intrusion pore volume of the silica particles is increased, the dentifrice RDA decreases. In order to prepare silica particles that perform in the desired RDA range, the correlations indicate the pack density values are desirably less than about 55 lb/ft$^3$ and the total mercury intrusion pore volume values are desirably greater than about 0.70 cc/g. Since these parameters can be controlled independently from the small pore porosity (BET surface area), silica particles may be produced with reduced pack density by introducing large pore porosity to lower RDA, while maintaining the low BET surface area values by reducing small pore porosity that are needed to achieve high stannous compatibility.

While not wishing to be bound by the following theory, it is believed that the improved surface area reduced silica particles of this invention can be produced, at least in part, by slowly filling in primarily the small pores of base silica particles defined by certain properties with additional silica material in a surface area reduction step. The resultant and unexpected combination of base silica particle properties and surface area reduced silica particle properties that were found particularly desirable are described in detail hereinbelow.

Surface Area Reduced Silica Particles

Consistent with aspects of the present invention, surface area reduced silica particles with improved stannous compatibility can have the following characteristics: (i) a BET surface area in a range from about 0.1 to about 7 m$^2$/g, (ii) a pack density in a range from about 35 to about 55 lb/ft$^3$, (iii) an Einlehner abrasion value in a range from about 8 to about 25 mg lost/100,000 revolutions, (iv) a total mercury intrusion pore volume in the range from about 0.7 to about 1.2 cc/g, and (v) a stannous compatibility in a range from about 70 to about 99%. In further aspects, stannous compatible surface area reduced silica particles consistent with the present invention also can have any of the characteristics or properties provided below, and in any combination.

In an aspect, the surface area reduced silica particles can have a very low surface area, generally a BET surface area ranging from about 0.1 to about 7 m$^2$/g. Often, the BET surface area can fall within a range from about 3 to about 6, from about 0.1 to about 5, from about 1 to about 7, or from about 1.5 to about 7 m$^2$/g. In further aspects, the BET surface area can be in a range from about 0.2 to about 5, from about 0.2 to about 3, from about 0.5 to about 5, from about 0.5 to about 6, from about 0.5 to about 5, or from about 0.5 to about 3.5 m$^2$/g, and the like. The BET surface area can also fall within a range from about 0.01 to about 10 m$^2$/g, from about 0.05 to about 8 m$^2$/g, from about 0.1 to about 9 m$^2$/g, or from about 1 to about 9 m$^2$/g. Other appropriate ranges for the BET surface area are readily apparent from this disclosure.

Additionally, the surface area reduced silica particles can be less abrasive, as reflected by an Einlehner abrasion value ranging from about 8 to about 25 mg lost/100,000 revolutions. For instance, the Einlehner abrasion value can be in a range from about 8 to about 20; alternatively, from about 10 to about 20; or alternatively, from about 15 to about 22 mg lost/100,000 revolutions. The Einlehner abrasion value can be in a range from about 30 to about 60 mg lost/100,000 revolutions. Other appropriate ranges for the Einlehner abrasion value are readily apparent from this disclosure.

These surface area reduced silica particles also have a relatively low pack density. In one aspect, the pack density can be in a range from about 35 to about 55 lb/ft$^3$. In another aspect, the pack density can be in a range from about 40 to about 55 lb/ft$^3$, from about 45 to about 55 lb/ft$^3$, or from about 40 to about 50 lb/ft$^3$. The pack density can be in the range from about 30 to about 60 lb/ft$^3$. Other appropriate ranges for the pack density are readily apparent from this disclosure.

Surface area reduced silica particles in accordance with aspects of this invention can have excellent stannous compatibility, excellent CPC compatibility, or both. Unexpectedly, it was found that silicas with good stannous compatibility generally also have good CPC compatibility, but silicas with good CPC compatibility do not necessarily also have good stannous compatibility. Typically, the surface area reduced silica particles described herein have a stannous compatibility from about 70 to about 99%, such as, for instance, from about 70 to about 95%, from about 70 to about 98%, from about 70 to about 90%, or from about 72 to about 95%, and the like. Additionally, the surface area reduced silica particles typically have a CPC compatibility from about 70 to about 99%, such as, for instance, from about 80 to about 98%, or from about 75 to about 95%, and the like. Other appropriate ranges for the stannous compatibility and CPC compatibility are readily apparent from this disclosure.

While not being limited thereto, the total mercury intrusion pore volume of the surface area reduced silica particles often can fall within a range from about 0.4 to about 1.2, from about 0.75 to about 1.05, from about 0.75 to about 0.9, or from about 0.9 to about 1.1 cc/g. The total mercury intrusion pore volume of the surface area reduced silica particles is from about 0.5 to about 1.7 cc/g, from about 0.6 to about 1.5 cc/g, or from about 0.4 to about 1.2 cc/g. Other appropriate ranges for the total mercury intrusion pore volume are readily apparent from this disclosure.

In an aspect, the surface area reduced silica particles can have a relatively small average particle size. Often, the median particle size (d50) and/or mean particle size (average) can fall within a range from about from about 1 to about 20, from about 1 to about 15, from about 2 to about 15, from about 2 to about 12, from about 2 to about 10, or from about 4 to about 10 μm, and the like. The median particle size (d50) and/or mean particle size (average) can fall within a range from about 1 to about 20 μm and from about 2 to about 15 μm. Other appropriate ranges for the mean and median particle sizes are readily apparent from this disclosure.

In another aspect, the surface area reduced silica particles can have relatively low oil absorption, relatively low water absorption, and/or very low CTAB surface area. For instance, the oil absorption can be in a range from about 25 to about 100 cc/100 g, from about 25 to about 75 cc/100 g, or from about 27 to about 60 cc/100 g. Additionally or alternatively, the water absorption can be in a range from about 50 to about 130 cc/100 g, from about 60 to about 120 cc/100 g, from about 65 to about 110 cc/100 g, or from about 75 to about 105 cc/100 g. Representative and non-limiting ranges for the CTAB surface include from 0 to about 10 $m^2/g$, from 0 to about 7 $m^2/g$, or from 0 to about 5 $m^2/g$. Other appropriate ranges for the oil absorption, the water absorption, and the CTAB surface area are readily apparent from this disclosure.

Additionally, the surface area reduced silica particles can have a substantially neutral pH that encompasses, for instance, a pH range of from about 5.5 to about 9, from about 6 to about 8, or from about 6.2 to about 7.8. Other appropriate ranges for the pH are readily apparent from this disclosure.

The surface area reduced silica particles can have a relatively narrow particle size distribution, with a weight percent of 325 mesh residue (amount retained in a 325 mesh sieve) generally less than or equal to about 1.5 wt. %. In some aspects, the 325 mesh residue can be less than or equal to about 1 wt. %, less than or equal to about 0.6 wt. %, less than or equal to about 0.3 wt. %, or less than or equal to about 0.2 wt. %.

In these and other aspects, any of the surface area reduced silica particles can be amorphous, can be synthetic, or can be both amorphous and synthetic. Moreover, the surface area reduced silica particles can comprise precipitated silica particles in particular aspects of this invention, although not limited thereto.

The Pellicle Cleaning Ratio (PCR) of a dentifrice containing surface area reduced silica particles is a measure of the cleaning characteristics of a dentifrice. The average PCR can be greater than about 60, greater than about 70, greater than 80, greater than about 100, greater than about 110, greater than about 120, and greater than 130. The average PCR of a dentifrice containing surface area reduced silica particles can be from about 60 to about 200, from about 70 to about 170, from about 80 to about 160, from about 90 to about 150, and from about 100 to about 140.

The Radioactive Dentine Abrasion (RDA) of a dentifrice containing surface area reduced silica particles is a measure of the abrasive safety of a dentifrice. The average RDA can be less than about 250, less than about 225, less than about 210, less than about 200. The average RDA of a dentifrice containing surface area reduced silica particles can be from about 70 to about 250, from about 70 to about 225, from about 70 to about 200, from about 90 to about 200, and from about 110 to about 200.

The average PCR/RDA ratio of a dentifrice containing surface area reduced silica, when incorporated into a dentifrice, may be at least 0.25, at least 0.5, at least 0.7, at least 0.9, and at least 1. The average PCR/RDA ratio may also be at least about 0.5. The average PCR/RDA ratio is a function of the particle size, shape, texture, hardness, and concentration.

The dentifrice compositions containing surface area reduced silica can have a soluble fluoride concentration from about 300 ppm to about 1500 ppm of fluoride ions, from about 450 ppm to about 1050 ppm, from about 500 ppm, to about 990 ppm, from about 700 ppm to about 935 ppm. A dentifrice composition containing a surface area reduced silica, can have a soluble fluoride concentration of greater than about 400 ppm fluoride ions, greater than about 600 ppm, greater than about 700 ppm, greater than about 800 ppm, greater than about 900 ppm, in greater than about 950 ppm, greater than about 1000 ppm, greater than 1300 ppm, greater than 1500 ppm, greater than 4500 ppm, greater than 5000 ppm, greater than 10,000 ppm, greater than 15,000 ppm, greater than 20,000 ppm, and greater than 25,000 ppm.

The dentifrice compositions may be free or substantially free of a fluoride ion source.

The percent soluble fluoride after 30 days at 40° C. can be greater than 70% of the initial fluoride concentration, greater than about 72%, greater than about 75%, greater than about 78%, greater than about 80%, greater than about 82%, greater than about 85%, greater than about 88%, greater than about 90%, and greater than about 95%.

The dentifrice compositions containing surface area reduced silica can have an extractable stannous ion concentration of from about 500 ppm to about 4000 ppm, from about 600 ppm to about 3500 ppm, from about 800 ppm to about 3000 ppm, from about 900 ppm to about 2500 ppm, from about 1000 ppm to about 2000 ppm, from about 1200 ppm to about 1900 ppm, and in another example from about 1400 ppm to about 1700 ppm. The dentifrice composition can contain an extractable stannous ion concentration from 300 ppm to about 10,000 ppm, from about 500 ppm to about 8000 ppm, from about 700 ppm to about 7000 ppm, from about 1000 ppm to about 6000 ppm. A dentifrice composition containing a surface area reduced silica, can have an extractable stannous ion concentration of greater than about 500 ppm stannous ions, greater than about 600 ppm, greater than about 700 ppm, greater than about 800 ppm, greater than about 900 ppm, greater than about 1000 ppm, greater than about 1200 ppm, greater than about 1500 ppm, greater than about 1700 ppm, greater than about 2000 ppm, greater than about 2200 ppm, greater than about 2500 ppm, greater than about 2700 ppm, greater than about 3000 ppm, greater than about 3200 ppm, greater than about 3300 ppm, greater than about 3400 ppm, and greater than about 3500 ppm. The extractable stannous ion concentration can be determined using the Extractable Stannous Ion Test Method for full compositions described herein.

The percent extractable stannous ion concentration after 30 days at 40° C. can be greater than 60% of the initial extractable stannous ion concentration, greater than 65%, greater than 70%, greater than 75%, greater than 80%, greater than 83%, greater than 85%, greater than 87%, greater than 90%, greater than 91%, greater than 92%, greater than 93%, greater than 95%, greater than 97%, greater than 98%, and greater than 99%. The percent extractable stannous ion concentration after 30 days at 40° C. can from about 55% to about 100% of the initial extractable stannous ion concentration, from about 63% to about 100%, from about 68% to about 100%, from about 72% to about 100%, from about 77% to about 100%, from about 83% to about 100%, from about 88% to about 100%, from about 91% to about 99%, from about 93% to about 99%, from about 95% to about 99%, and from about 96% to about 98%. The extractable stannous ion concentration can be determined using the Extractable Stannous Ion Test Method for full compositions described herein.

The dentifrice compositions can contain a zinc salt. The dentifrice compositions containing surface area reduced silica can have a soluble zinc ion concentration from about 900 ppm to about 1750 ppm zinc ions, from about 1000 ppm to about 1600 ppm, from about 1200 ppm to about 1500 ppm, and from about 1300 ppm to about 1400 ppm. The dentifrice composition containing surface area reduced silica can have a soluble zinc ion concentration from about 300 ppm to about 650 pm zinc ions, from about 400 ppm, to about 600 ppm, and from about 450 ppm to about 550 ppm. The dentifrice composition containing surface area reduced silica, can have a soluble zinc concentration greater than 500 ppm zinc ions, greater than 550 ppm, greater than 600 ppm, greater than 700 ppm, greater than 900 ppm, greater than 1000 ppm, greater than 1250 ppm, greater than 1400 ppm, and greater than 1500 ppm. The extractable zinc ion concentration can be determined using the Extractable Stannous Ion Test Method for full compositions described herein.

Processes for Producing Silica Particles

Processes for producing surface area reduced silicas particles are disclosed and described herein. Such processes to produce surface area reduced silica particles can comprise step (a) providing a mixture comprising water, sodium sulfate, and base silica particles characterized by (i) a base pack density in a range from about 25 to about 50 lb/ft$^3$, (ii) a base median particle size (d50) in a range from about 1 to about 10 microns, (iii) a base d95 particle size in a range from about 1 to about 20 microns, and (iv) a base total mercury intrusion pore volume in a range from about 0.8 to about 3 cc/g; step (b) adding to the mixture an alkali metal silicate and a mineral acid under surface area reduction conditions, wherein the alkali metal silicate is added to the mixture at an average silica addition rate in a range from about 0.2 to about 0.8 wt. % per minute and/or at a maximum silica addition rate of less than about 1.9 wt. % per minute; and step (c) ceasing the addition of the alkali metal silicate and continuing the addition of the mineral acid to the mixture at an average rate of addition of no more than 75% greater than an average rate of addition of the mineral acid in step (b) to adjust the pH of the mixture to within a range from about 5 to about 8.5; to produce surface area reduced silica particles characterized by (i) a BET surface area in a range from about 0.1 to about 7 m$^2$/g, (ii) a pack density in a range from about 35 to about 55 lb/ft$^3$, (iii) an Einlehner abrasion value in a range from about 8 to about 25 mg lost/100,000 revolutions, (iv) a total mercury intrusion pore volume in a range from about 0.7 to about 1.2 cc/g, and (v) a stannous compatibility in a range from about 70 to about 99%.

Generally, the features of these processes (e.g., any characteristics of the base silica particles, any characteristics of the surface area reduced silica particles, the alkali metal silicate and mineral acid materials, the conditions under which step (b) and step (c) are performed, among others) are independently described herein and these features can be combined in any combination to further describe the disclosed processes. Moreover, other process steps can be conducted before, during, and/or after any of the steps listed in the disclosed processes, unless stated otherwise. Additionally, surface area reduced silica particles produced in accordance with any of the disclosed processes are within the scope of this disclosure and are encompassed herein.

Base Particles—Step (a)

The base silica particles act as a precursor that directs the properties of the final stannous compatible surface area reduced silica particles. The base silica particles are a framework for silica material to be deposited thereupon during the surface area reduction step, and therefore the selection of the correct pack density, median particle size, particle size distribution, and total mercury intrusion pore volume of the base silica particles can be important. If the physical properties of the base silica particles would normally result in silica particles that are too abrasive, for example, for use in dentifrice applications, then the resulting surface area reduced silica particles likely also will be unacceptable. For example, if the particle size and particle pack density of the base silica particles are too high, unacceptably dense and abrasive surface area reduced silica particles likely will result. If the porosity—as measured by total mercury intrusion pore volume—is such that there are too few large pores, high density and unacceptably abrasive surface area reduced silica particles likely will result. In general, the correct base silica particles are needed in order to produce acceptable surface area reduced stannous compatible silica particles. Suitable base silica particles consistent with the present invention can have any of the characteristics or properties provided below, and in any combination.

In an aspect, the base silica particles have a base pack density in the range of from about 25 to about 50 lb/ft$^3$, from about 25 to about 45 lb/ft$^3$, from about 25 to about 40 lb/ft$^3$, or from about 30 to about 45 lb/ft$^3$, and the like. In an aspect, the base silica particles also can be characterized by a base median particle size (d50) in a range about 1 to about 10 μm, from about 2 to about 8 μm, from about 3 to about 7 μm, or from about 3 to about 6 μm, and the like. In an aspect, the d95 particle size of the base silica particles can fall within a range from about 1 to about 20 μm, from about 2 to about 20 μm, from about 1 to about 15 μm, from about 5 to about 20 μm, or from about 5 to about 15 μm. In an aspect, the base total mercury intruded pore volume of the base silica particles can be in the range of from about 0.8 to about 3 cc/g, from about 0.8 to about 2.5 cc/g, from about 0.9 to about 2.5 cc/g, or from about 0.9 to about 2 cc/g.

While not being limited thereto, the base silica particles in step (a) can have a BET surface area (a base BET surface area) in a range about 100 to about 500 m$^2$/g, from about 150 to about 350 m$^2$/g, from about 25 to about 150 m$^2$/g, or from about 25 to about 100 m$^2$/g, and the like. Generally, the higher BET surface area ranges apply to base silica particles prepared by the continuous loop reactor process described below, and the lower BET surface area ranges apply to base silica particles prepared using the ball/bead milling technique described below.

Additionally, the base silica particles, in certain aspects of this invention, can have an oil absorption in a range from about 60 to about 125 cc/100 g, from about 70 to about 110 cc/100 g, or from about 80 to about 115 cc/100 g. Additionally or alternatively, the base silica particles can have a water absorption (AbC) in a range from about 60 to about 130 cc/100 g, from about 70 to about 110 cc/100 g, or from about 80 to about 135 cc/100 g.

Referring to step (a) in the process for producing silica particles, the base silica particles of the mixture in step (a) can be produced in any manner by any suitable process, such as a precipitated silica production process. In a particular aspect consistent with this disclosure, the base silica particles can be produced by a process comprising forming the base silica particles in a continuous loop reactor (e.g., a continuous loop of one or more loop reactor pipes), such as described in U.S. Pat. Nos. 8,945,517 and 8,609,068, incorporated herein by reference in their entirety. In general, the continuous loop process involves (a) continuously feeding a mineral acid and an alkali metal silicate into a loop reaction zone comprising a stream of liquid medium, wherein at least a portion of the mineral acid and the alkali metal silicate react to form a silica product (e.g., the base silica particles) in the liquid medium of the loop reaction zone; (b) continuously recirculating the liquid medium through the loop reaction zone; and (c) continuously discharging from the loop reaction zone a portion of the liquid medium comprising the silica product. Typically, the feed locations of the mineral acid and the alkali metal silicate into the loop reaction zone are different, and the total feed rate of acid and silicate is proportional to, and often equal to, the discharge rate of the liquid medium containing the silica product. All or substantially of the contents within the loop reaction zone are recirculated, for instance, at a rate ranging from about 50 vol. % per minute (the recirculation rate, per minute, is one-half of the total volume of the contents) to about 1000 vol. % per minute (the recirculation rate, per minute, is ten times the total volume of the contents), or from about 75 vol. % per minute to about 500 vol. % per minute.

In another aspect consistent with this disclosure, the base silica particles of step (a) may be formed by using traditional precipitated silica production processes to form a reaction wet cake of precursor base silica particles, followed by making a slurry of the precursor base particles, and then by bead milling the wet precursor base particles to the desired base silica particle parameters described herein. An illustrative process is described in U.S. Pat. No. 6,419,174, incorporated herein by reference in its entirety. For instance, the precursor base particles (with water, sodium sulfate, pH of about 6 to about 8.5, temperature of about 80 to about 98° C., dependent upon pressure) can be produced in a batch reactor, such as a jacketed stirred tank reactor. The silica precursor base particles from the reactor can be concentrated using any suitable technique, an example of which is via the use of a filter press, to form the reaction wet cake of precursor base silica particles. In general, the silica precursor base particles can have any of the characteristics or properties provided below, and in any combination. In one aspect, the median particle size of the silica precursor base particles can fall within a range from about 10 to about 60 µm, or from about 15 to about 30 µm, and the like. Additionally or alternatively, the silica precursor base particles can have an oil absorption in a range from about 45 to about 90 cc/100 g, or from about 50 to about 65 cc/100 g. Additionally or alternatively, the silica precursor base particles can have a water absorption (AbC) in a range from about 50 to about 120 cc/100 g, or from about 60 to about 80 cc/100 g. Prior to bead milling, a slurry of the silica precursor base particles is made from the reaction wet cake. The precursor base particles are then bead milled in the slurry with any suitable milling media. Representative examples of suitable milling media include various ceramic beads, such as zirconia beads.

The continuous loop reactor process for preparing base silica particles, as described above, allows for the production of base silica particles with suitable particle size characteristics, without the need for any additional processing. Other techniques for preparing base silica particles utilize high shear devices attached to a batch reactor recirculation line and/or require the step of bead milling the silica slurry before the surface area reduction step. While bead milling a silica slurry can be used to achieve the desired base silica particle properties, additional processing steps are required for this approach (e.g., adjustment of solids for proper bead milling efficiency, followed by dilution and adjustment of the ionic strength before the surface area reduction step). With the Silverson high shear mixer approach, it is difficult to achieve a small and narrow particle size distribution, and overly abrasive particles can result (see Examples 9-17).

Surface Area Reduction—Step (b)

As disclosed herein, the surface area reduction step is performed so that the surface area resulting from small pores within the base silica particles are selectively filled in without also filling in the large pores and over densifying the surface area reduced silica particles. The base silica particles generally are provided unagglomerated for use during the surface area reduction step. Unagglomerated particles provide accessibility to allow the small pore porosity to be preferentially filled in, but with the final surface area reduced silica particles having suitable total mercury intrusion pore volume and pack density. In contrast, surface area reduction of agglomerated particles can result in large median particle sizes and high particle pack densities.

The addition rate of alkali metal silicate and mineral acid, time period, pH, and temperature are control variables during the surface area reduction step in order to achieve the desired surface area without increasing the particle size or dramatically increasing the density. While not wishing to be bound by the following theory, it is believed that when the surface area reduction step is performed at raw material addition rates that favor particle nucleation (i.e., too fast), new silica particles of higher surface area will be formed, and the small pore porosity will not be properly filled in. Additionally, if the surface area reduction step is carried out for a time period that is too short, the small pore porosity may not be sufficiently filled in, and the surface area of the base silica particles will not be sufficiently reduced to achieve silica particles compatible with stannous ions. Moreover, if the surface area reduction step is carried out for a time period that is too long, both the small pore and large pore porosity will be filled in, resulting in increases in the particles size, pack density, and abrasivity of the finished silica particles. Hence, the particulars of the surface area reduction step can impact whether low surface area silica particles that are compatible with stannous ions are produced, and whether these particles have desirable pack density, particle size, and abrasion characteristics.

In step (b), an alkali metal silicate and a mineral acid are added to the mixture comprising water, sodium sulfate, and base silica particles under any suitable surface area reduction conditions or any surface area reduction conditions disclosed herein. Consistent with aspects of this invention, the alkali metal silicate can be added to the mixture at an average silica addition rate in a range from about 0.2 to about 0.8 wt. % per minute, and/or at a maximum silica addition rate of less than about 1.9 wt. % per minute. The average value is determined by starting with the weight of base silica particles added (in kg), dividing by the addition time period (in minutes), and then normalizing by the total amount of surface area reduced silica particles (in kg) that is produced at the end of the surface area reduction step. The maximum silica addition rate is the largest average silica addition rate over any 5-minute period in the surface area reduction step. In some aspects, the alkali metal silicate can be added to the mixture at an average silica addition rate in a range from about 0.25 to about 0.7 wt. %, or from about 0.3 to about 0.55 wt. %, per minute. Additionally or alternatively, the maximum silica addition rate can be less than about 1.7 wt. % per minute, less than about 1.5 wt. % per minute, less than about 1.2 wt. % per minute, less than about 1 wt. % per minute, or less than about 0.9 wt. % per minute. Representative addition rate data are provided in the Examples that follow.

Illustrative and non-limiting examples of suitable alkali metal silicates include sodium silicate, potassium silicate, or mixtures thereof, and illustrative and non-limiting examples of suitable mineral acids include sulfuric acid, hydrochloric acid, nitric acid, phosphoric acid, or mixtures thereof. For instance, the alkali metal silicate can comprise sodium silicate and the mineral acid can comprise sulfuric acid. The specific methodology for the addition of the alkali metal silicate and the mineral acid to the mixture is not altogether limiting; for example, the alkali metal silicate and the mineral acid can be added in any order, whether simultaneously, sequentially, alternating, or combinations of these methodologies.

The surface area reduction conditions under which step (b) can be performed would be readily recognized by one of skill in the art in view of this disclosure and the representative examples provided hereinbelow. Nonetheless, in some aspects of this invention, the surface area reduction conditions of step (b) often can include a time period ranging from about 75 minutes to about 5 hours, from about 75 minutes to about 4 hours, from about 90 minutes to about 4 hours, from about 2 hours to about 5 hours, or from about 2 hours to about 4 hours; a pH ranging from about 9.2 to about 10.2, from about 9.3 to about 10, or from about 9.5 to about 9.8; and a temperature ranging from about 85 to about 100° C., from about 90 to about 100° C., or from about 95 to about 98° C.

Moreover, the surface area reduction step generally can be conducted under conditions sufficient to produce surface area reduced silica particles having a BET surface area at least about 25% less than the BET surface area of the base silica particles. More often, the surface area reduced silica particles have a BET surface area that is less than the BET surface area of the base silica particles by at least about 50% less, or by at least about 75% less, and in some aspects, at least about 80% less, at least about 90% less, at least about 95% less, at least about 97% less, or at least about 99% less.

Unexpectedly, and beneficially, it was found that a slow addition rate of the alkali metal silicate for the correct time at the correct conditions of pH (controlled by mineral acid addition) and temperature in the surface area reduction step can result in surface area reduced silica particles having an unexpected and beneficial combination of attributes, characterized by BET surface area, pack density, Einlehner abrasion value, total mercury intrusion volume, and stannous compatibility.

pH Adjustment—Step (c)

The general purpose of the pH adjustment step in the processes disclosed herein is to adjust the pH of the mixture (containing surface area reduced silica particles) to within a range from about 5 to about 8.5, by adding only mineral acid to the mixture. Since there is a significant percentage of soluble alkali metal silicate present in the mixture at the end of the surface area reduction step, the pH adjustment step typically is carefully controlled to minimize any impact on the distribution of porosity of the finished stannous compatible (and surface area reduced) silica particles. In some aspects, the average rate of addition of the mineral acid in step (c) is no more than 75% greater than an average rate of addition of the mineral acid in step (b), while in other aspects, the average rate of addition of the mineral acid in step (c) is no more than 50% greater, no more than 25% greater, or no more than 10% greater, than the average rate of addition of the mineral acid in step (b). Often, the average rate of addition of mineral acid in step (c) is approximately the same, or less than, the average rate of addition of the mineral acid in step (b).

While not wishing to be bound by the following theory, if the acid rate is too fast during the pH adjustment step, new silica particles may form with surface areas higher than that of the surface area reduced silica particles, resulting in an overall increase in BET surface area of the silica particles. In some of the examples that follow, a faster acid flow rate was used during the pH adjustment step, likely resulting in an increase in small pore porosity. However, for CPC compatibility, this increased acid rate was not detrimental to the production of CPC compatible silica particles, because CPC likely could not access the smaller pores that were formed.

While not being limited thereto, the pH of the reaction mixture at the end of the batch often is adjusted to within a range from about 5 to about 8.5, and in some cases, from about 5.5 to about 8, or from about 6 to about 8, for suitability in end-use dentifrice and other applications.

After the pH adjustment step, and optionally, the processes disclosed herein can further include a filtering step to isolate the surface area reduced silica particles, a washing step to wash the surface area reduced silica particles, a drying step (e.g., spray drying) to dry the surface area reduced silica particles, or any combination of the filtering, washing, and drying steps, and performed in any suitable sequence.

Dentifrice Compositions

The surface area reduced silica particles can be used in an oral care composition, such as a dentifrice composition. The compositions can contain a stannous ion source and an abrasive. The surface area reduced silica particles can be used instead of or in combination with abrasives that are commonly used in dentifrices.

The oral care composition can contain a stannous ion source. The stannous ion source can be a stannous salt selected from the group consisting of stannous fluoride, stannous chloride dihydrate, stannous acetate, stannous gluconate, stannous oxalate, stannous sulfate, stannous lactate, and stannous tartrate. The stannous ion sources are stannous fluoride and/or stannous chloride dihydrate. The combined stannous salts can be present in an amount of from about 0.1% to about 11%, by weight of the total composition. The stannous salts are present in an amount of from about 0.05% to about 7%, from about 0.1% to about 5%, from about 0.25% to about 3%, and from about 0.5% to about 1.5% by weight of the total composition. Formulations can include stannous levels, provided by stannous fluoride and/or stannous stabilizing salts including stannous chloride, ranging from about 3,000 ppm to about 15,000 ppm stannous ions in the total composition. The dentifrice can contain 0.454% stannous fluoride and/or 0.56% stannous chloride. The dentifrice composition can contain less than 0.454% stannous fluoride and/or less than 0.56% stannous chloride. The compositions may not contain stannous chloride. Dentifrices containing stannous salts, particularly stannous fluoride and stannous chloride, are described in U.S. Pat. No. 5,004,597 to Majeti et al., incorporated herein in its entirety. Other descriptions of stannous salts are found in U.S. Pat. No. 5,578,293 issued to Prencipe et al. and in U.S. Pat. No. 5,281,410 issued to Lukacovic et al., incorporated herein in its entirety. In addition to the stannous ion source, other ingredients needed to stabilize the stannous may also be included, such as the ingredients described in Majeti et al. and Prencipe et al.

The oral compositions can also contain a soluble fluoride source capable of providing bioavailable and efficacious fluoride ions. Soluble fluoride ion sources can be selected from the group consisting of sodium fluoride, stannous fluoride, indium fluoride, sodium monofluorophosphate, amine fluoride, silver fluoride, and combinations thereof. The composition can contain stannous fluoride and this ingredient may serve as both a/the stannous source and fluoride source. Norris et al., U.S. Pat. No. 2,946,725, issued Jul. 26, 1960, and Widder et al., U.S. Pat. No. 3,678,154 issued Jul. 18, 1972, disclose such fluoride sources as well as others. Both patents are incorporated herein by reference in their entirety.

The present compositions may contain a soluble fluoride ion source capable of providing from about 50 ppm to about 3500 ppm, or from about 500 ppm to about 3000 ppm of free fluoride ions. To deliver the desired amount of fluoride ions, fluoride ion sources may be present in the total oral composition at an amount of from about 0.1% to about 5%, from about 0.2% to about 1%, or from about 0.3% to about 0.60%), by weight of the total composition delivered to the oral cavity.

The oral care compositions can include a polymeric surface active agent (MSA).

The polymeric mineral surface active agents that can be incorporated into the oral care compositions described herein include polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly (acrylamide), poly(methacrylate), poly(ethacrylate), poly (hydroxyalkylmethacrylate), poly(vinyl alcohol), poly(maleic anhydride), poly(maleate) poly(amide), poly(ethylene amine), poly(ethylene glycol), poly(propylene glycol), poly (vinyl acetate) and poly(vinyl benzyl chloride); carboxy-substituted polymers; and mixtures thereof. Suitable polymeric surface active agents include the carboxy-substituted alcohol polymers described in U.S. Pat. Nos. 5,292,501; 5,093,170; 5,009,882; and 4,939,284; all to Degenhardt et al. and the diphosphonate-derivatized polymers in U.S. Pat. No. 5,011,913 to Benedict et al. Suitable structures can include copolymers of acrylic acid or methacrylic acid with phosphonates. And the composition can include diphosphonate modified polyacrylic acid.

Suitable phosphonate-containing polymers are described in U.S. Pat. No. 5,980,776 to Zakikhani, et al., incorporated herein in its entirety.

The polymeric mineral surface active agent can be a polyphosphate. A polyphosphate is generally understood to consist of two or more phosphate molecules arranged primarily in a linear configuration, although some cyclic derivatives may be present. The inorganic polyphosphate salts can include tetrapolyphosphate and hexametaphosphate, among others. Polyphosphates larger than tetrapolyphosphate usually occur as amorphous glassy materials. The composition can include linear "glassy" polyphosphates having the formula:

$$XO(XPO_3)_nX$$

wherein X is sodium or potassium and n averages from about 6 to about 125. In some examples, the polyphosphates are manufactured by FMC Corporation (Philadelphia, Pa., USA), which are commercially known as Sodaphos (n≈6), Hexaphos (n≈13), and Glass H (n≈21). The composition can include Glass H.

The amount of mineral surface agent required is an effective amount which will bind the stannous, permit adequate antimicrobial activity, reduce dental stain and formulation astringency, and be capable of reducing dental calculus. An effective amount of a mineral surface active agent will typically be from about 1% to about 35%, from about 2% to about 30%, from about 5% to about 25%, from about 6% to about 20%, by weight of the total oral composition.

The oral care composition can also contain an aqueous carrier. Such materials are well known in the art and are readily chosen by one skilled in the art based on the physical and aesthetic properties desired for the compositions being prepared. Aqueous carriers typically comprise from about 50% to about 99%, preferably from about 70% to about 98%, and more preferably from about 90% to about 95%, by weight of the oral composition.

Water employed in the preparation of commercially suitable oral compositions should preferably be of low ion content and free of organic impurities. If the oral composition comprises a polyphosphate having an average chain length of about 4 or more, the composition or phase containing the polyphosphate will comprise a lower level of water, generally up to about 20% total water. The total water content is from about 2% to about 20%, from about 4% to about 15%, or from about 5% to about 12%, by weight of the oral composition. The composition can have a higher level of water, for instance from about 10% to about 99%, from about 20% to about 95%, from about 20% to about 90%, from about 30% to about 80%, from about 40% to about 70%, from about 50% to about 60%, and the like. The amounts of water include the free water which is added plus that which is introduced with other materials, such as with sorbitol, silica, surfactant solutions, and/or color solutions.

The present compositions may contain a buffering agent. Buffering agents, as used herein, refer to agents that can be used to adjust the pH of the compositions to a range of about pH 3.0 to about pH 10. The oral composition can have a slurry pH of from about 3.0 to about 7.0, from about 3.25 to about 6.0, and from about 3.5 to about 5.5. The oral care composition can have an alkaline slurry pH, for instance greater than about 8, greater than about 9, or greater than about 10.

The buffering agents can include alkali metal hydroxides, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and/or sodium citrate. The buffering agents can include acetic acid, sodium acetate, citric acid, sodium citrate, lactate, benzoic acid and/or sodium benzoate. Buffering agents can be at a level of from about 0.1% to about 30%, from about 1% to about 10%, or from about 1.5% to about 3%, by weight of the composition.

The composition can include an anticalculus agent, which can include pyrophosphates, tripolyphosphates, and/or synthetic anionic polymers including polyacrylates and copolymers of maleic anhydride or acid and methyl vinyl ether, such as Gantrez™ as described in U.S. Pat. No. 4,627,977 to Gaffar et al., and polyamino propane sulfonic acid (AMPS). Also included are zinc citrate trihydrate, diphosphonates such as EHDP and AHP and polypeptides such as polyaspartic and polyglutamic acids, and mixtures thereof.

The composition can include an abrasive polishing material in addition to the surface area reduced silica. Typical abrasive polishing materials can include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used. If the oral composition or particular phase comprises a polyphosphate having an average chain length of about 4 or more, calcium containing abrasives and alumina are not preferred abrasives. The most preferred abrasive is silica.

The composition can include precipitated silica and/or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. The types of silica dental abrasives that can be useful in the compositions of the present invention are described in more detail in Wason, U.S. Pat. No. 4,340,583, issued Jul. 29, 1982, incorporated herein by reference. Silica abrasives are also described in Rice, U.S. Pat. Nos. 5,589,160; 5,603,920; 5,651,958; 5,658,553; and 5,716,601; herein incorporated by reference. The total abrasive level in the oral compositions can be from about 0.1% to about 70%, from about 0.5% to about 65%, from about 2% to 60%, from about 6% to about 55% by weight of the composition, and the like. The oral care compositions can contain from about 10% to about 50% of abrasive, by weight of the oral composition.

The composition can include from about 1% to about 50%, from about 3% to about 40%, from about 5% to about 35%, from about 5% to about 30%, from about 7% to about 27%, from about 10% to about 25%, from about 11% to about 20%, or from about 13% to about 18%, surface area reduced silica particles, by weight of the composition. The composition can contain from about 1% to about 25%, from about 3% to about 20%, or from about 5% to about 15%, surface area reduced silica particles, by weight of the composition.

The composition may include a peroxide source. The peroxide source can be selected from the group consisting of hydrogen peroxide, calcium peroxide, urea peroxide, and mixtures thereof. The present composition may contain from about 0.01% to about 10%, from about 0.1% to about 5%, from about 0.2% to about 3%, or from about 0.3% to about 0.8% of a peroxide source, by weight of the oral composition.

The present invention may also include an alkali metal bicarbonate salt, for example sodium bicarbonate. The present composition may contain from about 0.5% to about 50%, from about 0.5% to about 30%, from about 2% to about 20%, or from about 5% to about 18% of an alkali metal bicarbonate salt, by weight of the oral composition.

The composition can include a thickening agent, such as carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.1% to about 15%, by weight of the oral composition.

The oral care composition can include a humectant, which can include glycerin, sorbitol, polyethylene glycol, propylene glycol, xylitol, and other edible polyhydric alcohols. The composition can contain from about 0% to 70%, or from about 15% to 55%, humectant, by weight of the oral composition.

The present compositions may also comprise surfactants. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms.

Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants can include poloxamers (sold under trade name Pluronic), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The nonionic surfactant poloxamer 407 can be used. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of the suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, from about 0.5% to about 8%, or from about 1% to about 6%, by weight of the composition.

Titanium dioxide may also be added to the present composition. Titanium dioxide can generally comprise from about 0.25% to about 5%, by weight of the composition.

Coloring agents may also be added to the present composition. The coloring agent may be in the form of an aqueous solution, for instance 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, mardoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents in addition to the stannous to provide antimicrobial benefits. Included among such antimicrobial agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey, incorporated herein by reference. Other antimicrobials such as copper bisglycinate, copper glycinate, zinc citrate, and zinc lactate may also be included. Also useful are enzymes, including endoglyciosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, to Gieske et al., incorporated herein by reference. Specific antimicrobial agents include chlorhexidine, triclosan, triclosan monophosphate, and flavor oils such as thymol. Triclosan and other agents of this type are disclosed in U.S. Pat. No. 5,015,466, issued to Parran, Jr. et al. and U.S. Pat. No. 4,894,220, to Nabi et al., incorporated herein by reference. These agents may be present at levels of from about 0.01%, to about 1.5%, by weight of the oral composition.

The antimicrobial benefit can also be delivered from natural sources such as plant extracts including hops and extracts of thereof, magnolia bark extracts, including honokiol and magnolol, other botanical and essential oils and combinations thereof.

The oral composition can help protect against cavities, gingivitis, plaque, sensitivity, tartar, staining, and acid erosion and can also provide whitening benefits and freshen breath. Methods of treatment include preparing an oral composition containing the stannous ion source and the surface area reduced silica particles and administering the composition to the subject. Administering to the subject may be defined as having the oral composition contact the tooth surfaces of the subject by brushing with a dentifrice or rinsing with a dentifrice slurry. Administration may also be by contacting the topical oral gel, mouth rinse, denture product, mouth spray, oral tablet, lozenge, or chewing gum with the tooth surfaces. The subject may be any person or lower animal whose tooth surfaces contact the oral composition.

Example A below shows an aqueous dentifrice formulation containing surface area reduced silica particles (Silica).

| Example A | (wt. %) |
|---|---|
| Water | 25.200 |
| Sorbitol Solution USP[1] | 37.832 |
| Flavor | 1.200 |
| Hydroxyethyl Cellulose 250M 420 NF | 0.720 |
| Sodium Lauryl Sulfate Solution (29%) | 5.000 |
| Stannous Fluoride | 0.454 |
| Xanthan Gum | 0.540 |
| Saccharin Sodium USP Granular, High Moisture[2] | 0.800 |
| Sodium Gluconate | 1.064 |
| Silica | 15.000 |
| Carrageenan | 1.080 |
| Zinc Lactate Dihydrate | 1.000 |
| Gantrez ™ S-95 (35% Solution)[3] | 5.71 |
| Xylitol, USP-NF | 3.00 |
| Sodium Hydroxide (Dilution 50%) FCC | 1.40 |

[1]Sorbitol Solution USP is an aqueous solution containing 70% sorbitol
[2]Saccharin Sodium USP Granular, high moisture contains up to 14% water
[3]Available from Ashland ®, Wilmington, Delaware, USA Example A was prepared as follows: In a separate container, the hydroxyethyl cellulose (HEC) was dispersed into the flavor and mixed until the mixture appeared homogeneous. Then a jacketed mix tank was set to approximately 30° C. and a first portion of the sorbitol was added to the tank. Then the HEC/flavor blend was added and incorporated with agitation and homogenization followed by the second portion of sorbitol and water, which were incorporated with homogenization. Then, the saccharin, stannous fluoride, sodium gluconate, xanthan gum, and carrageenan were mixed in a separate container and then these powders were added to the vessel and homogenized. After the homogenization was completed, the agitator was stopped and the vacuum was released. Then, the zinc lactate dehydrate, Gantrez™ S-95 and xylitol were added to the vessel and with agitation and homogenization and then the mixture we deaerated. Then, the Silica was added to the mixture and the mixture was mixed and deaerated. Then, the sodium lauryl sulfate was added to the vessel and the mixture was agitated at the highest possible vacuum. Then, the sodium hydroxide was added to the vessel and mixed under vacuum. After mixing was complete, the batch was homogenized and then mixed and deaerated. The vacuum was released and Example A was formed.

Example B below shows a non-aqueous dentifrice formulation with surface area reduced silica particles (Silica).

| Example B | (wt. %) |
|---|---|
| Glycerin USP (99.7% Vegetable Base) | 47.244 |
| Polyethylene Glycol 300 USP-NF | 7.000 |
| Propylene Glycol USP Grade | 7.000 |
| Sodium Lauryl Sulfate Solution (29%) | 3.400 |
| Stannous Fluoride | 0.454 |
| Xanthan Gum | 0.250 |
| Saccharin Sodium USP Granular, High Moisture | 0.500 |
| Sodium Gluconate | 0.652 |
| Silica | 15.000 |
| Carrageenan | 0.600 |
| Zinc Lactate Dihydrate | 2.500 |
| Sodium Hexametaphosphate[4] | 13.00 |
| Dye | 0.30 |
| Tribasic Sodium Phosphate Dodecahydrate | 1.10 |
| Flavor | 1.00 |

[4]Available from ICL Performance Products, St. Louis, Missouri, USA

Example B was prepared as follows: The glycerin was pre-weighed and added to the vessel. With the homogenizer running, the xanthan gum and carrageenan were added to the vessel and homogenized. Then, the sodium lauryl sulfate solution is added to the vessel and agitated and homogenized. Then, the agitation is stopped and the vacuum is released, and the vessel lid is opened and the polyethylene glycol, propylene glycol, remaining glycerin, and color and flavor are added to the vessel, the lid was closed and the agitator and vacuum were restarted. Then, the Silica was added to the vessel and mixed. Then, the saccharin, zinc lactate, stannous fluoride, and sodium gluconate were added to the vessel and homogenized. Then, the sodium hexametaphosphate and tribasic sodium phosphate were added to the vessel and the mixture is mixed at the highest possible vacuum. After five minutes, the agitation was stopped, the vacuum was released, and the lid was lifted and the tribasic sodium phosphate was added and the lid was closed and the agitator and vacuum were restored and the mixture was mixed under vacuum. Finally, the product was mixed and deareated at the highest possible vacuum for at least five minutes. Then the Example B was discharged from the product discharge valve.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The BET surface areas and the pore volumes (total mercury intrusion pore volumes) disclosed herein were determined on a Micromeritics TriStar II 3020 V1.03 using, respectively, the BET nitrogen adsorption method of Brunaur et al., J. Am. Chem. Soc., 60, 309 (1938), and BJH Desorption isotherms with a Halsey Faas Correction, Halsey, G. D., J. Chem. Phys. (1948), 16, pp. 931, and such techniques are well known to those skilled in the art.

CTAB surface areas disclosed herein were determined by absorption of CTAB (cetyltrimethylammonium bromide) on the silica surface, the excess separated by centrifugation and the quantity determined by titration with sodium lauryl sulfate using a surfactant electrode. Specifically, about 0.5 grams of the silica particles were placed in a 250-mL beaker with 100 mL CTAB solution (5.5 g/L), mixed on an electric stir plate for 1 hour, then centrifuged for 30 min at 10,000 RPM. One mL of 10% Triton X-100 was added to 5 mL of the clear supernatant in a 100-mL beaker. The pH was adjusted to 3-3.5 with 0.1 N HCl and the specimen was titrated with 0.01 M sodium lauryl sulfate using a surfactant electrode (Brinkmann SUR1501-DL) to determine the endpoint.

The median particle size (d50) refers to the particle size for which 50% of the sample has a smaller size and 50% of the sample has a larger size. Median particle size (d50), mean particle size (average), d90, and d95 were determined via the laser diffraction method using a Horiba LA 300 instrument. Dry particles were submitted to the instrument for analysis, except for base silica particles, which were submitted as a (wet) slurry in water.

For pour density and pack density, 20 grams of the sample were placed into a 250 mL graduated cylinder with a flat rubber bottom. The initial volume was recorded and used to calculate the pour density by dividing it into the weight of sample used. The cylinder was then placed onto a tap density machine where it was rotated on a cam at 60 RPM. The cam is designed to raise and drop the cylinder a distance of 5.715 cm once per second, until the sample volume is constant, typically for 15 min. This final volume is recorded and used to calculate the packed density by dividing it into the weight of sample used.

The Einlehner abrasion value is a measure of the hardness/abrasiveness of silica particles, and is described in detail in U.S. Pat. No. 6,616,916, incorporated herein by reference, and involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams of brass lost from the Fourdrinier wire screen per 100,000 revolutions (mg lost/100,000 revolutions).

CPC compatibility (%) was determined as follows. 27.00 grams of a 0.3% solution of CPC (cetylpyridinium chloride) were added to a 3.00 g sample of the silica to be tested. The silica was previously dried at 105° C. to 150° C. to a moisture content of 2% or less, and the pH of the sample was measured to ensure the 5% pH was between 5.5 and 7.5. The mixture was shaken for a period of 10 minutes. Accelerated aging testing requires agitation of the test specimen for 1 week at 140° C. After agitation was complete, the sample was centrifuged and 5 mL of the supernatant was passed through a 0.45 µm PTFE milli-pore filter and discarded. An additional 2.00 g of supernatant was then passed through the same 0.45 µm PTFE milli-pore filter and then added to a vial containing 38.00 g of distilled water. After mixing, an aliquot of the sample was placed in a cuvette (methyl methacrylate) and the U.V. absorbance was measured at 268 nm. Water was used as a blank. The % CPC compatibility was determined by expressing as a percentage the absorbance of the sample to that of a CPC standard solution prepared by this procedure with the exception that no silica was added.

Stannous compatibility (%) was determined as follows. A stock solution containing 431.11 g of 70% sorbitol, 63.62 g of de-oxygenated deionized water, 2.27 g of stannous chloride dihydrate, and 3.00 g of sodium gluconate was prepared. 34.00 g of the stock solution was added to a 50 mL centrifuge tube containing 6.00 g of the silica sample to be tested. The centrifuge tube was placed on a rotating wheel at 5 RPM and was aged for 1 week at 40° C. After aging, the centrifuge tube was centrifuged at 12,000 RPM for 10 minutes, and the stannous concentration in the supernatant was determined by ICP-OES (inductively coupled plasma optical emission spectrometer). The stannous compatibility was determined by expressing the stannous concentration of the sample as a percentage of the stannous concentration of a solution prepared by the same procedure, but with no silica added.

Oil absorption values were determined in accordance with the rub-out method described in ASTM D281 using linseed oil (cc oil absorbed per 100 g of the particles). Generally, a higher oil absorption level indicates a particle with a higher level of large pore porosity, also described as higher structure.

Water absorption values were determined with an Absorptometer "C" torque rheometer from C.W. Brabender Instruments, Inc. Approximately ⅓ of a cup of the silica sample was transferred to the mixing chamber of the Absorptometer and mixed at 150 RPM. Water then was added at a rate of 6 mL/min, and the torque required to mix the powder was recorded. As water is absorbed by the powder, the torque will reach a maximum as the powder transforms from free-flowing to a paste. The total volume of water added when the maximum torque was reached was then standardized to the quantity of water that can be absorbed by 100 g of powder. Since the powder was used on an as received basis (not previously dried), the free moisture value of the powder was used to calculate a "moisture corrected water AbC value" by the following equation.

$$\text{Water Absorption} = \frac{\text{water absorbed (cc)} + \% \text{ moisture}}{(100 \text{ (g)} - \% \text{ moisture})/100}$$

The Absorptometer is commonly used to determine the oil number of carbon black in compliance with ASTM D 2414 methods B and C and ASTM D 3493.

The pH values disclosed herein (5% pH) were determined in an aqueous system containing 5 wt. % solids in deionized water using a pH meter.

The 325 mesh residue (wt. %) of the silica sample was measured utilizing a U.S. Standard Sieve No. 325, with 44 micron or 0.0017 inch openings (stainless steel wire cloth), by weighing a 10.0 gram sample to the nearest 0.1 gram into the cup of a 1 quart Hamilton mixer (Model No. 30), adding approximately 170 mL of distilled or deionized water, and stirring the slurry for at least 7 min. The mixture was transferred onto the 325 mesh screen and water was sprayed directly onto the screen at a pressure of 20 psig for two minutes, with the spray head held about four to six inches from the screen. The remaining residue was then transferred to a watch glass, dried in an oven at 150° C. for 15 min, then cooled, and weighed on an analytical balance.

The PCR (Pellicle Cleaning Ratio) cleaning values were determined by a slightly modified version of the PCR test described in "In Vitro Removal of Stain with Dentifrice", G. K. Stookey, T. A. Burkhard and B. R. Schemerhorn, J. Dental Research, 61, 1236-9, 1982. Cleaning was assessed in vitro by use of the modified pellicle cleaning ratio test. This test was identical to that described by Stookey et al. with the following modifications: (1) a clear artificial pellicle film was applied to bovine chips prior to application of the stained film, (2) solution heating was used rather than radiative heating during film application, (3) the number of brush strokes was reduced to 800 strokes and (4) the slurry concentration was 1 part dentifrice to 3 parts water. The test was repeated at least three times and the mean was calculated to get an average PCR.

The Radioactive Dentin Abrasion (RDA) values were determined by International Organization for Standardization (ISO) 11609: 2010(E) Annex B. The test was repeated at least three times and the mean was calculated to get an average RDA.

The Extractable Stannous Ion and Extractable Zinc Ion Test Method was used to determine the extractable stannous ion concentration in supernatant (ESCS) and extractable zinc ion concentration in supernatant (EZCS) using inductively coupled plasma optical emission spectrometry. For the purposes of this invention, any tin measured by this method is considered to be in the form of stannous ion ($Sn^{2+}$), and any zinc measured by this method is considered to be in the form of soluble zinc ion. Single-point external-standard calibration is used for both tin and zinc, and a gallium internal standard is used for both samples and standards. If the fraction of insolubles (w/w) in the full dentifrice composition is known, extractable stannous ion concentration in full composition (ESCFC) and extractable zinc ion concentration in full composition (EZCFC) are also determined.

One entire tube (or container) of dentifrice is homogenized with a laboratory SpeedMixer (such as the DAC250, Flacktek, Inc., or equivalent) for 120 seconds at 1500 rpm. A slurry of 1 part dentifrice to 3 parts water (by mass) is prepared by adding 2.00 g of the homogenized sample and 6.00 g deionized water to a centrifuge tube (appropriately sized for total sample volume) containing 10 glass beads (4 mm diameter). The sample is mixed with a vortex mixer for 60 minutes at 1200 rpm. The resulting slurry is immediately centrifuged at 21,000 RCF for 10 minutes. Samples tubes are removed from the centrifuge within 5 minutes of completion of centrifugation. The supernatant is decanted into a 15-mL screw-cap sample tube. For samples that do not have a clearly delineated liquid/solid interface, a maximal quantity of the supernatant is decanted such that any gelatinous or transition layer remains in the centrifuge tube along with any centrifugate present.

The decanted supernatant is mixed well by shaking vigorously by hand. One aliquot (approximately 0.5 g, but mass recorded precisely to within ±0.001 g) is transferred to a 50-mL conical polypropylene tube. To this tube are added 2.5 mL of concentrated nitric acid (~70% w/w) and 2.5 mL concentrated hydrochloric acid (35% w/w). The sample tube is covered with a polypropylene watch glass and placed in a preheated hot block digester sized appropriately for the conical polypropylene tube (such as DigiPrep, SCP Science) at 90° C. for 30 minutes. The watch glass is then rinsed with less than 5 mL deionized water 3 times, adding the rinsate to the sample tube. As an internal standard, 2.00 mL of 100 μg/mL gallium standard (such as is available from Inorganic Ventures or equivalent) is delivered to the tube, and the total volume of the tube is brought to 50 mL with deionized water.

Tin and zinc standard solutions are each prepared at 10.0 ppm using commercially available stock solutions (such as is available from Inorganic Ventures or equivalent) in an acid matrix of 5% (v/v) concentrated nitric acid and 5% (v/v) concentrated hydrochloric acid with 4.00 ppm gallium as an internal standard.

Standards and samples are analyzed using a dual-view inductively coupled plasma optical emission spectrometer (such as Optima 8300 ICP-OES, Perkin Elmer, Inc., or equivalent) equipped with either a cross flow nebulizer and double pass spray chamber (such as a Gem tip cross flow nebulizer, Perkin Elmer, Inc., or equivalent) or an enhanced parallel-path nebulizer (such as MiraMist, Glass Expansion or equivalent) nebulizer and a Tracey cyclonic spray chamber (such as that available from Glass Expansion or equivalent). The ICP-OES system is optimized for the maximum Mg II (280 nm)/Mg I (285 nm) ratio. Tin is determined at 189.9 nm in axial mode. Zinc is determined at 213.8 nm in radial mode. Gallium is determined in both axial and radial modes at 417.2 nm. Quantification for tin and zinc is performed using a single point calibration curve prepared at 10 ppm using gallium as an internal standard.

From the ICP-OES sample analysis, extractable stannous ion concentration in supernatant (μg/g) is calculated from:

$$ESCS\ [\mu g/g] = \frac{\text{conc. Sn from } ICP\text{-}OES \text{ sample } [\mu g/mL] \times 50\ mL}{\text{mass of supernatant aliquot } [g]}$$

From the ICP-OES sample analysis, extractable zinc ion concentration in supernatant (μg/g) is calculated from:

$$EZCS\ [\mu g/g] = \frac{\text{conc. Zn from } ICP\text{-}OES \text{ sample } [\mu g/mL] \times 50\ mL}{\text{mass of supernatant aliquot } [g]}$$

ESCS and EZCS are reported to three significant figures in units of μg/g.

Dentifrice often contains particles essentially insoluble in water ("insolubles"), including but not limited to compounds such as silica, titania, mica, cetyl alcohol, and stearyl alcohol. If the fraction (w/w) of insolubles in full dentifrice composition is known, extractable stannous ion concentration (w/w) in full composition (ppm) is calculated via ESCFC [ppm]=(4−fraction of insolubles in full formula)×ESCS and the fraction (w/w) of insolubles in full dentifrice composition is known, extractable zinc ion concentration (w/w) in full composition (ppm) is calculated via EZCFC [ppm]=(4−fraction of insolubles in full formula)×EZCS ESCFC and EZCFC are reported to three significant figures in units of ppm.

The % extractable stannous ion concentration is determined storing the composition in a standard opaque dentifrice tube for thirty days at 40° C. and measuring the ESCFC, and then dividing its value with a total theoretical stannous level in the composition and multiplying by a 100 (to express as %).

Examples 1-8

Comparative Silica Particles with Low BET Surface Areas

Table I summarize certain properties of comparative silica materials having low BET surface areas. Despite the low BET surface areas, these silica materials are deficient in one more properties selected from low CPC compatibility, high Einlehner abrasion, high total mercury intrusion pore volume, high CTAB surface area, high oil absorption, high 325 mesh residue, and/or high pack density.

Examples 9-17

Silica Particles Produced with Low BET Surface Areas by the Silverson Method

Examples 9-17 were produced with low BET surface areas, but in an effort to improve upon some of the deficiencies noted in Examples 1-8, the acid addition rate that was used to reduce the pH after the silicate addition was complete was kept at the same rate that was used during the surface area reduction step of the batch. This was done in an attempt to reduce the amount of porosity resulting from small pores.

For Example 9, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 198 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 10, 38 L of sodium silicate (2.65 MR, 13.3%) was added to a reactor and was heated to 95° C. with stirring at 50 RPM. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min During this time, the pH was kept in the 9.7 (+/−0.2) range. If needed, the acid rate was adjusted to maintain the desired pH. After 198 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS. The silica slurry was then pH adjusted to 5.0 (+/−0.2) with the addition of sulfuric acid and was then spray dried to a target moisture of 5%.

For Example 11, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 168 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 12, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 138 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 13, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 108 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 14, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 78 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 15, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 63 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 16, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 198 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS and was spray dried to a target moisture of 5%.

For Example 17, 38 L of sodium silicate (2.65 MR, 13.3%) was added to a reactor and was heated to 95° C. with stirring at 50 RPM and recirculation at 80 L/min. A Silverson high shear in-line mixer attached to the recirculation line of the reactor was operated at 3600 RPM. Once 95° C. was reached, sodium silicate (2.65 MR, 13.3%) and sulfuric acid (11.4%) were added at 8.1 L/min and 3.6 L/min, respectively. After 48 minutes, the Silverson in-line mixer was stopped, and the sodium silicate (2.65 MR, 13.3%) and sulfuric acid (11.4%) were reduced to 2.3 L/min and 1.2 L/min. During this time, the pH was kept in the 9.7 (+/−0.2) range. If needed, the acid rate was adjusted to maintain the desired pH. After 198 minutes (total) had passed, the flow of sodium silicate was stopped and the pH was adjusted to 5 with continued flow of sulfuric acid (11.4%) at 1.2 L/min. The batch was then digested for 20 minutes at pH 5.0 (+/−0.2), and was then filtered and washed to a conductivity of <1500 μS. The pH of the silica slurry was then adjusted to 5.0 (+/−0.2) with sulfuric acid and was then spray dried to a target moisture of 5%.

Figure 3:
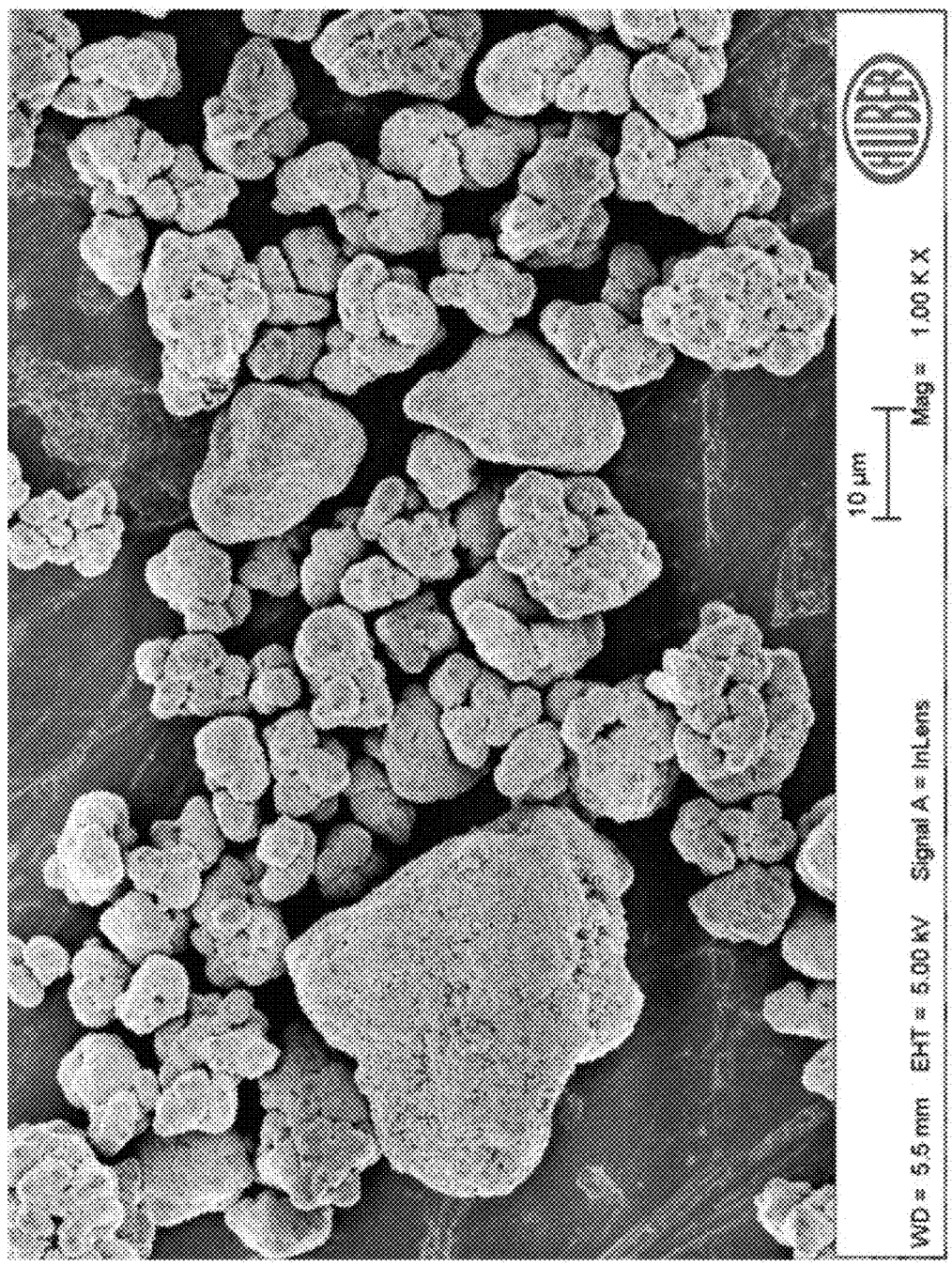
FIG. 3 is a Scanning Electron Micrograph of the silica of Example 10.
Figure 4:
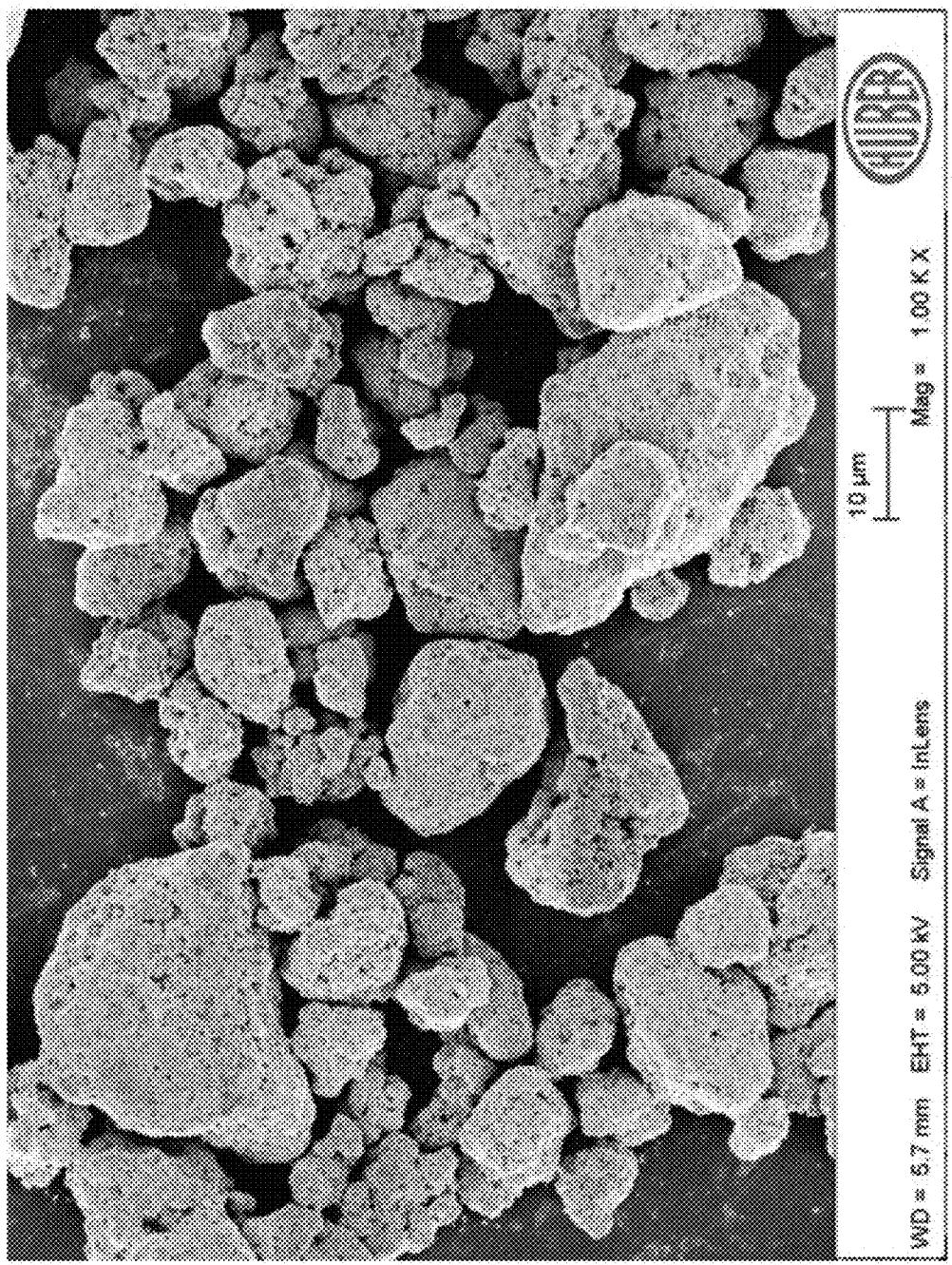
FIG. 4 is a Scanning Electron Micrograph of the silica of Example 15.

Table II summarizes certain properties of the silica particles produced in Examples 9-17. Some of the silicas produced in Examples 9-17 resulted in improved stannous compatibility values (Examples 9-11 and 16); however, the Einlehner abrasion values and pack densities for these samples were unacceptably high. For instance, when Einlehner values are too high—typically, greater than 25 mg lost/100,000 revolutions—the silica particles are very abrasive to both dentin, and the processing equipment used to produce both the silica particles and the dentifrice/toothpaste formulations. Examination of SEM images demonstrated a wide particle size distribution, with a range of both large and small particles, and non-spherical particle morphology. For Examples 9-17, representative SEM images are provided as FIG. 3 (Example 10) and FIG. 4 (Example 15).

Examples 18-22

Silica Particles Produced with Low BET Surface Areas by the Continuous Loop Reactor Method In these examples, a continuous loop reactor process (see e.g., U.S. Pat. Nos. 8,945,517 and 8,609,068) was used to produce base silica particles, followed by a subsequent surface area reduction of the base silica particles to produce silica particles with a BET surface area in the desired range. The loop reactor process was used to produce the base silica particles with a more spherical morphology and a tighter particle size distribution (e.g., less 325 mesh residue in the final silica product) than in the previous examples.

For Example 18A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 95° C. Once 95° C. was reached, sodium silicate (2.65 MR, 20.0%) and sulfuric acid (17.1%) were then continuously added at rates of 1.50 L/min and 0.78 L/min, respectively. If needed, the acid rate was adjusted to maintain a reaction pH of 7.5. After 20 minutes of running, the silica that was collected was discarded (purge material) and 300 L of silica slurry was then collected.

In Example 18B, the surface area was reduced. The 300 L slurry of base silica particles from Example 18A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 1.87 L/min and 1.0 L/min, respectively. If needed, the acid rate was adjusted to maintain pH 9.5 (+/−0.2). After 30 minutes from the start of the co-addition of the silicate and acid, the sodium silicate (2.65 MR, 20.0%) and sulfuric acid (17.1%) rates were adjusted to 1.00 L/min and 0.60 L/min, respectively. After a total time of 45 minutes, the flow of sodium silicate was stopped and the pH was adjusted to 7 with continued addition of sulfuric acid (17.1%) at 0.60 L/min. The batch was digested for 10 minutes at pH 7, and was then filtered and washed to a conductivity of <1500 µS. Prior to drying, the pH of the silica slurry was adjusted to 5 with sulfuric acid and was spray dried to a target moisture of 5%.

For Example 19A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 95° C. Once 95° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 19B, the surface area was reduced. The 500 L slurry of base silica particles from Example 19A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 1.66 L/min and 0.80 L/min, respectively. If needed, the acid rate was adjusted to maintain pH 9.5 (+/−0.2). After a total time of 15 minutes from the start of co-addition, the flow of sodium silicate was stopped and the pH was adjusted to 7 with continued addition of sulfuric acid (17.1%) at 0.80 L/min. The batch was digested for 15 minutes at pH 7, and was then filtered and washed to a conductivity of <1500 µS. Prior to drying, the pH of the silica slurry was adjusted to 5 with sulfuric acid and was spray dried to a target moisture of 5%.

For Example 20A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 95° C. Once 95° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 20B, the surface area was reduced. The 500 L slurry of base silica particles from Example 20A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 3.11 L/min and 1.50 L/min, respectively. If needed, the acid rate was adjusted to maintain pH 9.5 (+/−0.2). After 15 minutes from the start of the co-addition of the silicate and acid, the sodium silicate (2.65 MR, 20.0%) and sulfuric acid (17.1%) rates were adjusted to 1.66 L/min and 0.80 L/min, respectively. After a total time of 30 minutes, the flow of sodium silicate was stopped and the pH was adjusted to 7 with continued addition of sulfuric acid (17.1%) at 0.60 L/min. The batch was digested for 15 minutes at pH 7, and was then filtered and washed to a conductivity of <1500 µS. Prior to drying, the pH of the silica slurry was adjusted to 5 with sulfuric acid and was spray dried to a target moisture of 5%.

For Example 21A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 95° C. Once 95° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 21B, the surface area was reduced. The 500 L slurry of base silica particles from Example 21A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 3.11 L/min and 1.50 L/min, respectively. If needed, the acid rate was adjusted to maintain pH 9.5 (+/−0.2). After 30 minutes from the start of the co-addition of the silicate and acid, the sodium silicate (2.65 MR, 20.0%) and sulfuric acid (17.1%) rates were adjusted to 1.66 L/min and 0.80 L/min, respectively. After a total time of 45 minutes, the flow of sodium silicate was stopped and the pH was adjusted to 7 with continued addition of sulfuric acid (17.1%) at 0.60 L/min. The batch was digested for 15 minutes at pH 7, and was then filtered and washed to a conductivity of <1500 µS. Prior to drying, the pH of the silica slurry was adjusted to 5 with sulfuric acid and was spray dried to a target moisture of 5%.

For Example 22A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 95° C. Once 95° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 22B, the surface area was reduced. The 500 L slurry of base silica particles from Example 22A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 3.11 L/min and 1.50 L/min, respectively. If needed, the acid rate was adjusted to maintain pH 9.5 (+/−0.2). After 45 minutes from the start of the co-addition of the silicate and acid, the sodium silicate (2.65 MR, 20.0%) and sulfuric acid (17.1%) rates were adjusted to 1.66 L/min and 0.80 L/min, respectively. After a total time of 60 minutes, the flow of sodium silicate was stopped and the pH was adjusted to 7 with continued addition of sulfuric acid (17.1%) at 0.60 L/min. The batch was digested for 15 minutes at pH 7, and was then filtered and washed to a conductivity of <1500 µS. Prior to drying, the pH of the silica slurry was adjusted to 5 with sulfuric acid and was spray dried to a target moisture of 5%.

Figure 5:
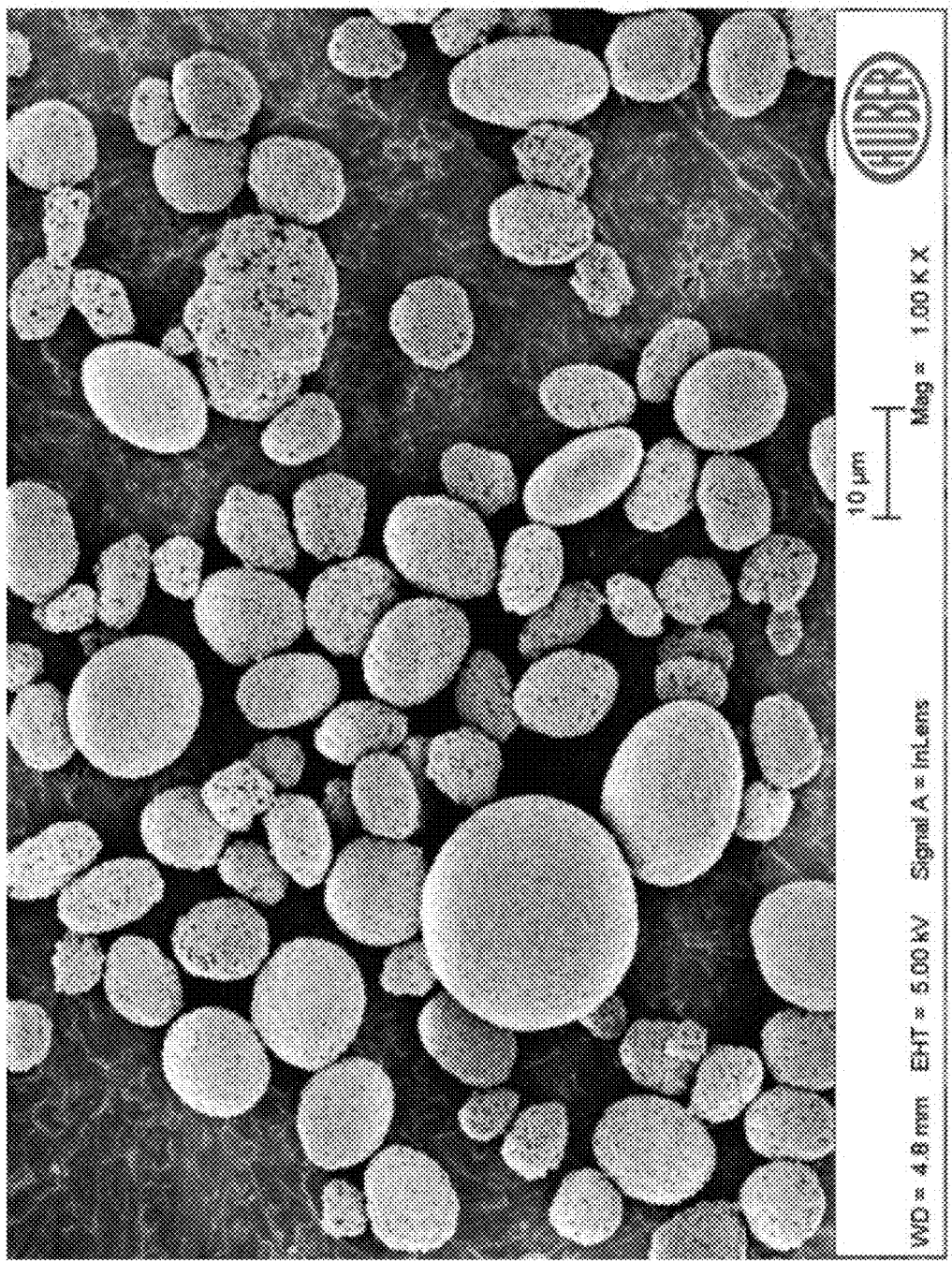
FIG. 5 is a Scanning Electron Micrograph of the silica of Example 19B.
Figure 6:
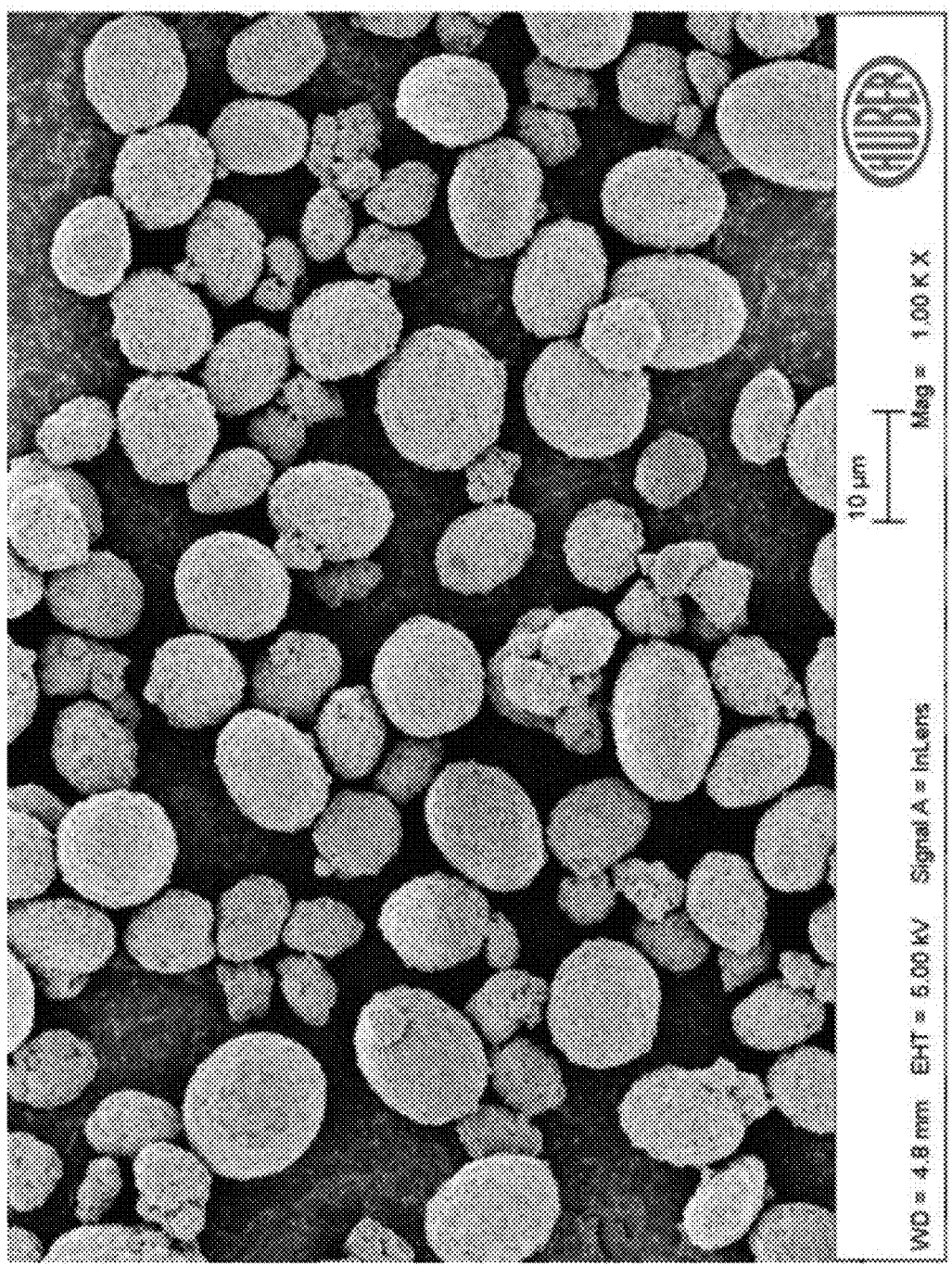
FIG. 6 is a Scanning Electron Micrograph of the silica of Example 22B.

Table III summarizes certain properties of the silica particles produced in Examples 18-22. Pack density, Einlehner abrasion, 325 mesh residue, and particle size for Examples 18B-22B were reduced from that of Examples 9-17, while largely maintaining acceptable stannous compatibility, CPC compatibility, and BET surface area. Interestingly, the total mercury intrusion pore volumes were in the 0.6-0.7 cc/g range. Examination of SEM images demonstrated a narrow particle size distribution and spherical particle morphology. For Examples 18-22, representative SEM images are provided as FIG. 5 (Example 19B) and FIG. 6 (Example 22B).

Examples 23-25

Silica Particles Produced with Low BET Surface Areas by the Continuous Loop Reactor Method Similar to Examples 18-22, these examples utilized a continuous loop reactor process to produce the base silica particles, followed by a subsequent surface area reduction of the base silica particles to produce silica particles with a BET surface area in the desired range.

For Example 23A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 23B, the surface area was reduced. The 500 L silica slurry from Example 23A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 3.11 L/min and 1.5 L/min, respectively. If needed, the acid rate was adjusted to maintain pH 9.5 (+/−0.2). After 60 minutes from the start of the co-addition of the silicate and acid, the sodium silicate (2.65 MR, 20.0%) and sulfuric acid (17.1%) rates were adjusted to 1.66 L/min and 0.80 L/min, respectively. After a total time of 75 minutes, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 µS. Prior to drying, the pH of the silica slurry was adjusted to 5 with sulfuric acid and was spray dried to a target moisture of 5%.

For Example 24A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 50° C. Once 50° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 24B, the surface area was reduced. The 500 L silica slurry from Example 24A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 3.11 L/min and 1.5 L/min, respectively. If needed, the acid rate was adjusted to maintain pH 9.5 (+/−0.2). After 60 minutes from the start of the co-addition of the silicate and acid, the sodium silicate (2.65 MR, 20.0%) and sulfuric acid (17.1%) rates were adjusted to 1.66 L/min and 0.80 L/min, respectively. After a total time of 90 minutes, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 µS. Prior to drying, the pH of the silica slurry was adjusted to 5 with sulfuric acid and was spray dried to a target moisture of 5%.

For Example 25A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 25B, the surface area was reduced. The 500 L silica slurry from Example 25A was added to a batch reactor and was heated to 95° C. with stirring at 80 RPM. Sodium silicate (2.65 MR, 20.0%) was added to the reactor until a pH of 9.5 (+/−0.2) was reached. Once pH 9.5 (+/−0.2) was reached, sodium silicate (2.65 MR, 20.0%) and sulfuric acid (17.1%) were added at rates of 1.66 L/min and 0.80 L/min, respectively. If needed, the acid rate was adjusted to maintain pH 9.5 (+/−0.2). After a total time of 180 minutes, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

Figure 7:
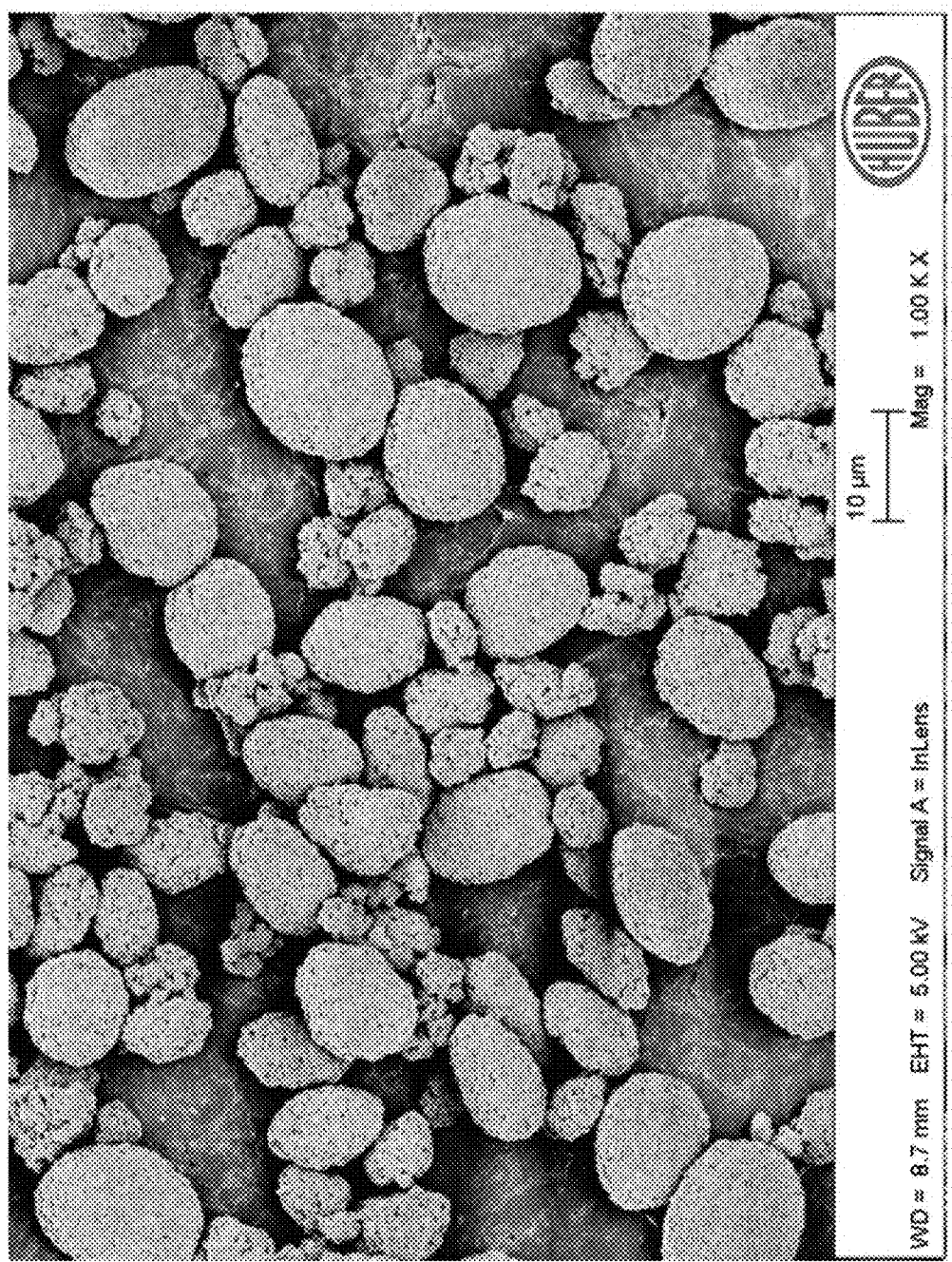
FIG. 7 is a Scanning Electron Micrograph of the silica of Example 25B.

Table IV summarizes certain properties of the silica particles produced in Examples 23-25. As compared to Examples 18B-22B, Examples 23B-25B had higher total mercury intrusion pore volumes and lower pack densities. Additionally, each of Examples 23B-25B had excellent stannous compatibility and CPC compatibility. Also, as shown in Table IV, the significant amount of surface area reduction is evident: from 302 to 0.6 m²/g (Examples 23A-23B) and from 280 to 1.3 m²/g (Examples 24A-24B). In the surface area reduction step, the average silica addition rate for Examples 23B-25B ranged from 0.36 to 0.66 wt. % per minute, and the maximum silica addition rate ranged from 0.50 to 0.92 wt. % per minute. Examination of SEM images demonstrated a narrow particle size distribution and spherical particle morphology. For Examples 23-25, a representative SEM image is provided as FIG. 7 (Example 25B).

Examples 26-30

Silica Particles Produced with Low BET Surface Areas by the Continuous Loop Reactor Method Examples 26-30 were performed similarly to those of Examples 23-25. For Example 26A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 26B, the surface area was reduced. The 500 L slurry of base silica particles from Example 26A and 65 L of sodium silicate (2.65 MR, 20.0%) were added to a batch reactor and were heated to 95° C. with stirring at 80 RPM. Once 95° C. was reached, sodium silicate (2.65 MR, 20.0%) and sulfuric acid (17.1%) were added at rates of 3.11 L/min and 1.4 L/min, respectively. After 60 minutes from the start of the co-addition of silicate and acid, the sodium silicate (2.65 MR, 20.0%) and sulfuric acid (17.1%) rates were adjusted to 1.66 L/min and 0.80 L/min, respectively. After a total time of 75 minutes, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

For Example 27A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 27B, the surface area was reduced. The 500 L slurry of base silica particles from Example 27A and 65 L of sodium silicate (2.65 MR, 20.0%) were added to a batch reactor and were heated to 95° C. with stirring at 80 RPM. Once 95° C. was reached, sodium silicate (2.65 MR, 20.0%) and sulfuric acid (17.1%) were added at rates of 1.66 L/min and 0.8 L/min, respectively. After 188 minutes from the start of the co-addition of silicate and acid, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

For Example 28A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 28B, the surface area was reduced. The 500 L slurry of base silica particles from Example 28A and 65 L of sodium silicate (2.65 MR, 20.0%) were added to a batch reactor and were heated to 95° C. with stirring at 80 RPM. Once 95° C. was reached, sodium silicate (2.65 MR, 20.0%) and sulfuric acid (17.1%) were added at rates of 1.66 L/min and 0.8 L/min, respectively. After 161 minutes from the start of the co-addition of silicate and acid, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

For Example 29A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 29B, the surface area was reduced. The 500 L slurry of base silica particles from Example 29A and 65 L of sodium silicate (2.65 MR, 20.0%) were added to a batch reactor and were heated to 95° C. with stirring at 80 RPM. Once 95° C. was reached, sodium silicate (2.65 MR, 20.0%) and sulfuric acid (17.1%) were added at rates of 1.66 L/min and 0.8 L/min, respectively. After 150 minutes from the start of the co-addition of silicate and acid, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

For Example 30A, approximately 15 L of previously-made silica slurry at approximately 10% solids was added to a recirculation loop reactor and was circulated at 80 L/min with a high shear Silverson in-line mixer operating at 3600 RPM. The continuous loop reactor was then heated to 60° C. Once 60° C. was reached, sodium silicate (2.65 MR, 20.0%) and sulfuric acid (17.1%) were then continuously added at rates of 1.70 L/min and 0.87 L/min, respectively. If needed, the acid rate was adjusted to maintain a reaction pH of 7.5. After 20 minutes of running, the silica that was collected was discarded (purge material) and 500 L of silica slurry was then collected.

In Example 30B, the surface area was reduced. The 500 L slurry of base silica particles from Example 30A and 65 L of sodium silicate (2.65 MR, 20.0%) were added to a batch reactor and were heated to 95° C. with stirring at 80 RPM. Once 95° C. was reached, sodium silicate (2.65 MR, 20.0%) and sulfuric acid (17.1%) were added at rates of 1.66 L/min and 0.8 L/min, respectively. After 135 minutes from the start of the co-addition of silicate and acid, the flow of sodium silicate was stopped and the pH was adjusted to 7 with continued addition of sulfuric acid (17.1%) at 0.80 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

Figure 8:
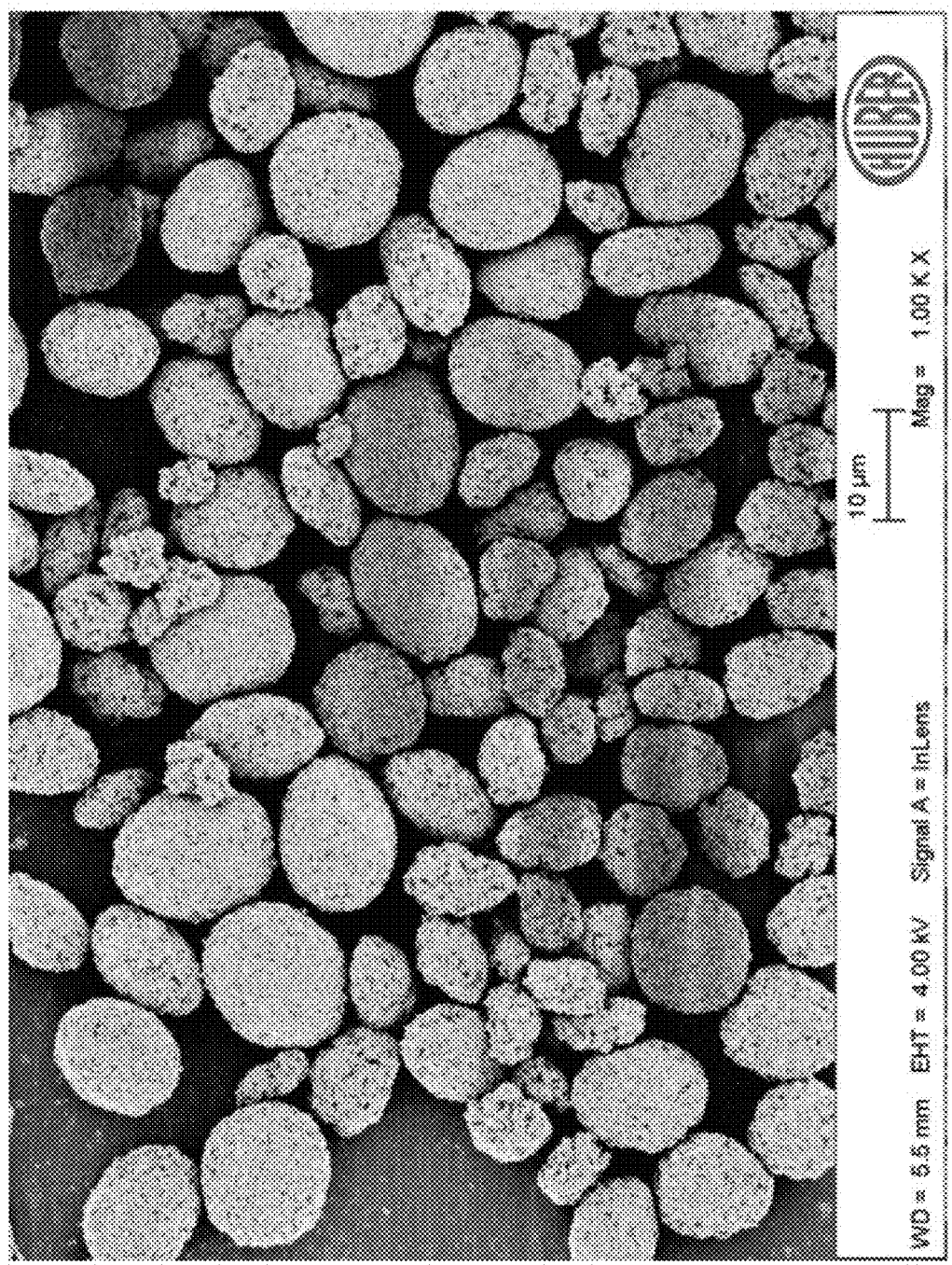
FIG. 8 is a Scanning Electron Micrograph of the silica of Example 28B.

Table V summarizes certain properties of the silica particles produced in Examples 26-30. Similar to Examples 23B-25B, Examples 27B-30B demonstrate an unexpected and beneficial combination of BET surface area, pack density, Einlehner abrasion, stannous compatibility, and/or CPC compatibility. Also, as shown in Table V, the significant amount of surface area reduction is evident: from 232 to 8 m²/g (Examples 26A-26B). In the surface area reduction step, the average silica addition rate for Examples 27B-30B was approximately 0.37 wt. % per minute, and the maximum silica addition rate was 0.50 wt. % per minute. Examination of SEM images demonstrated a narrow particle size distribution and spherical particle morphology. For Examples 26-30, a representative SEM image is provided as FIG. 8 (Example 28B).

Examples 31-33

Silica Particles Produced with Low BET Surface Areas by the Bead Milling Method

In Examples 31-33, a batch containing precursor base silica particles was produced in a reactor, followed by bead milling to produce base silica particles, and then a subsequent surface area reduction of the base silica particles to produce silica particles with a BET surface area in the desired range, but lacking other desired properties.

For Example 31A, 69 L of sodium silicate (2.65 MR, 13.3%) was added to a reactor and heated to 85° C. with stirring at 60 RPM and recirculation at 80 L/min Once 85° C. was reached, sodium silicate (2.65 MR, 13.3%) and sulfuric acid (11.4%) were added simultaneously at 14.7 L/min and 6.5 L/min, respectively, for 47 minutes. After the 47 minutes, the flow of sodium silicate was stopped and the pH was adjusted to pH 5.8 (+/−0.2) with the continued flow of sulfuric acid (11.4%) at 6.5 L/min. The batch was then digested for 20 minutes at 93° C. while maintaining pH 5.8 (+/−0.2). The batch was then de-watered in a filter press and bead milled to a 325 mesh residue of 0% and a median particle size of less than 10 μm.

Next in Example 31B, the surface area was reduced, starting with 45 L of a bead milled intermediate silica slurry (31% solids) and 180 L of water added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 4.5 L/min and 2.2 L/min, respectively, for 30 minutes. If needed, the acid rate was adjusted to maintain the batch pH at 9.75 (+/−0.2). After 30 minutes, the flow of sodium silicate (2.65 MR, 13.3%) and sulfuric acid (11.4%) were reduced to 4.2 L/min and 2.0 L/min, respectively. After 60 minutes, the flow of sodium silicate and sulfuric acid were reduced to 3.6 L/min and 1.7 L/min, respectively. After 90 minutes, the flow of sodium silicate and sulfuric acid were reduced to 3.1 L/min and 1.5 L/min, respectively. After 120 minutes, the flow of sodium silicate and sulfuric acid were reduced to 2.3 L/min and 1.2 L/min, respectively. After 150 minutes, the flow of sodium silicate was stopped and the pH was reduced to 6.0 (+/−0.2) with continued flow of sulfuric acid at 1.2 L/min Once the desired pH was reached, the batch was digested for 20 minutes while maintaining pH 6.0 (+/−0.2). The batch was then filtered and washed to a conductivity of <1500 μS. The pH of the silica slurry was then adjusted to 5.0 (+/−0.2) with sulfuric acid and was spray dried to a target moisture of 5%.

For Example 32A, 8 L of sodium silicate (2.65 MR, 20.0%) and 89 L of deionized water were added to a reactor and heated to 85° C. with stirring at 60 RPM and recirculation at 80 L/min Once 85° C. was reached, sodium silicate (2.65 MR, 20.0%) and sulfuric acid (17.1%) were added simultaneously at 12.5 L/min and 5.0 L/min, respectively, for 48 minutes. After the 48 minutes, the flow of sodium silicate was stopped and the pH was adjusted to pH 5.8 (+/−0.2) with the continued flow of sulfuric acid (17.1%) at 5.0 L/min. The batch was then digested for 15 minutes at 93° C. while maintaining pH 5.8 (+/−0.2). The batch was then de-watered with a filter press and bead milled to a 325 mesh residue of 0% and a median particle size of less than 10 μm.

In Example 32B, the surface area was reduced. 45 L of bead-milled intermediate silica slurry of Example 32A (31% solids) and 180 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 4.2 L/min and 2.0 L/min, respectively, for 30 minutes. If needed, the acid rate was adjusted to maintain the batch pH at 9.75 (+/−0.2). After 30 minutes, the flow of sodium silicate (2.65 MR, 13.3%) and sulfuric acid (11.4%) were reduced to 3.6 L/min and 1.7 L/min, respectively. After 60 minutes, the flow of sodium silicate and sulfuric acid were reduced to 3.1 L/min and 1.5 L/min, respectively. After 90 minutes, the flow of sodium silicate and sulfuric acid were reduced to 2.3 L/min and 1.2 L/min, respectively. After 135 minutes, the flow of sodium silicate was stopped and the pH was reduced to 6.0 (+/−0.2) with continued flow of sulfuric acid at 1.2 L/min. Once the desired pH was reached, the batch was digested for 20 minutes while maintaining pH 6.0 (+/−0.2). The batch was then filtered and washed to a conductivity of <1500 μS. The pH of the silica slurry was then adjusted to 5.0 (+/−0.2) with sulfuric acid and was spray dried to a target moisture of 5%.

For Example 33A, 50 L of sodium silicate (2.65 MR, 20.0%) and 162 L of deionized water were added to a reactor and heated to 85° C. with stirring at 60 RPM and recirculation at 80 L/min Once 85° C. was reached, sodium silicate (2.65 MR, 20.0%) and sulfuric acid (17.1%) were added simultaneously at 11.6 L/min and 4.7 L/min, respectively, for 47 minutes. After the 47 minutes, the flow of sodium silicate was stopped and the pH was adjusted to pH 5.8 (+/−0.2) with the continued flow of sulfuric acid (17.1%) at 4.7 L/min. The batch was then digested for 20 minutes at 93° C. while maintaining pH 5.8 (+/−0.2). The batch was then de-watered with a filter press and bead milled to a 325 mesh residue of 0% and a median particle size of less than 10 μm.

In Example 33B, the surface area was reduced. 45 L of bead-milled intermediate silica slurry of Example 33A (31% solids) and 180 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 4.5 L/min and 2.2 L/min, respectively, for 30 minutes. If needed, the acid rate was adjusted to maintain the batch pH at 9.75 (+/−0.2). After 30 minutes, the flow of sodium silicate (2.65 MR, 13.3%) and sulfuric acid (11.4%) were reduced to 4.2 L/min and 2.0 L/min, respectively. After 60 minutes, the flow of sodium silicate and sulfuric acid were reduced to 3.6 L/min and 1.7 L/min, respectively. After 90 minutes, the flow of sodium silicate and sulfuric acid were reduced to 3.1 L/min and 1.5 L/min, respectively. After 120 minutes, the flow of sodium silicate and sulfuric acid were reduced to 2.3 L/min and 1.2 L/min, respectively. After 165 minutes, the flow of sodium silicate was stopped and the pH was reduced to 6.0 (+/−0.2) with continued flow of sulfuric acid at 1.2 L/min Once the desired pH was reached, the batch was digested for 20 minutes while maintaining pH 6.0 (+/−0.2). The batch was then filtered and washed to a conductivity of <1500 μS. The pH of the silica slurry was then adjusted to 5.0 (+/−0.2) with sulfuric acid and was spray dried to a target moisture of 5%.

Table VI summarizes certain properties of the silica materials produced in Examples 31-33. The silica particles of Example 31B had an improved particle size distribution (lower 325 mesh residue and lower Einlehner abrasion), slightly reduced stannous compatibility and CPC compatibility, but with a significant increase in pack density. In Examples 32A and 32B, the surface area reduction step did not result in desired silica particles because the surface area reduction occurred too rapidly (e.g., the average silica addition rate was 0.97 wt. % per minute, and the maximum silica addition rate was 2.46 wt. % per minute), resulting in the formation of new particles as shown by the high BET surface area and low stannous compatibility. In Examples 33A and 33B, the surface area reduction step did not result in desired silica particles because of too much surface area reduction, resulting in high pack density and high Einlehner abrasion values.

Examples 34-39

Silica Particles Produced with Low BET Surface Areas by the Bead Milling Method

Examples 34-39 were performed similarly to those of Examples 32-33. For Example 34A, 29 L of sodium silicate (2.65 MR, 20.0%) and 126 L of deionized water were added to a reactor and heated to 85° C. with stirring at 60 RPM and recirculation at 80 L/min. Once 85° C. was reached, sodium silicate (2.65 MR, 20.0%) and sulfuric acid (17.1%) were added simultaneously at 12.1 L/min and 4.8 L/min, respectively, for 47 minutes. After the 47 minutes, the flow of sodium silicate was stopped and the pH was adjusted to pH 5.8 (+/−0.2) with the continued flow of sulfuric acid (17.1%) at 4.8 L/min. The batch was then digested for 20 minutes at 93° C. while maintaining pH 5.8 (+/−0.2). The batch was then de-watered with a filter press and was bead milled to a 325 mesh residue of 0% and a median particle size of less than 10 μm.

In Example 34B, the surface area was reduced. 100 L of bead-milled base silica particle slurry of Example 34A and 380 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 2.3 L/min and 1.0 L/min, respectively, for 220 minutes. If needed, the acid rate was adjusted to maintain the batch pH at 9.75 (+/−0.2). After 220 minutes, the flow of sodium silicate was stopped and the pH was reduced to 6.0 (+/−0.2) with continued flow of sulfuric acid at 1.0 L/min. Once the desired pH was reached, the batch was digested for 20 minutes while maintaining pH 6.0 (+/−0.2). The batch was then filtered and washed to a conductivity of <1500 μS. The pH of the surface area reduced silica slurry was then adjusted to 5.0 (+/−0.2) with sulfuric acid and was spray dried to a target moisture of 5%.

For Example 35A, 8 L of sodium silicate (2.65 MR, 20.0%) and 89 L of deionized water were added to a reactor and heated to 85° C. with stirring at 60 RPM and recirculation at 80 L/min Once 85° C. was reached, sodium silicate (2.65 MR, 20.0%) and sulfuric acid (17.1%) were added simultaneously at 12.5 L/min and 5.0 L/min, respectively, for 47 minutes. After the 47 minutes, the flow of sodium silicate was stopped and the pH was adjusted to pH 5.8 (+/−0.2) with the continued flow of sulfuric acid (17.1%) at 5.0 L/min. The batch was then digested for 20 minutes at 93° C. while maintaining pH 5.8 (+/−0.2). The batch was then de-watered with a filter press and bead milled to a 325 mesh residue of 0% and a median particle size of less than 10 μm.

In Example 35B, the surface area was reduced. 100 L of bead-milled base silica particle slurry of Example 35A and 380 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 2.3 L/min and 1.0 L/min, respectively, for 170 minutes. If needed, the acid rate was adjusted to maintain the batch pH at 9.75 (+/−0.2). After 170 minutes, the flow of sodium silicate was stopped and the pH was reduced to 6.0 (+/−0.2) with continued flow of sulfuric acid at 1.0 L/min. Once the desired pH was reached, the batch was digested for 20 minutes while maintaining pH 6.0 (+/−0.2). The batch was then filtered and washed to a conductivity of <1500 μS. The pH of the surface area reduced silica slurry was then adjusted to 5.0 (+/−0.2) with sulfuric acid and was spray dried to a target moisture of 5%.

For Example 36A, 50 L of sodium silicate (2.65 MR, 20.0%) and 162 L of deionized water were added to a reactor and heated to 85° C. with stirring at 60 RPM and recirculation at 80 L/min Once 85° C. was reached, sodium silicate (2.65 MR, 20.0%) and sulfuric acid (17.1%) were added simultaneously at 11.6 L/min and 4.7 L/min, respectively, for 47 minutes. After the 47 minutes, the flow of sodium silicate was stopped and the pH was adjusted to pH 5.8 (+/−0.2) with the continued flow of sulfuric acid (17.1%) at 5.0 L/min. The batch was then digested for 20 minutes at 93° C. while maintaining pH 5.8 (+/−0.2). The batch was then de-watered with a filter press and bead milled to a target particle size of 5 μm.

In Example 36B, the surface area was reduced. 100 L of bead-milled base silica particle slurry of Example 36A (31% solids) and 380 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 2.3 L/min and 1.0 L/min, respectively, for 210 minutes. After 210 minutes, the silicate (2.65 MR, 13.3%) and sulfuric acid (11.4%) rates were adjusted to 1.15 L/min and 0.5 L/min, respectively. If needed, the acid rate was adjusted to maintain the batch pH at 9.75 (+/−0.2). After 282 minutes (total), the flow of sodium silicate was stopped and the pH was reduced to 6.0 (+/−0.2) with continued flow of sulfuric acid at 0.5 L/min. Once the desired pH was reached, the batch was digested for 20 minutes while maintaining pH 6.0 (+/−0.2). The batch was then filtered and washed to a conductivity of <1500 μS. The pH of the surface area reduced silica slurry was then adjusted to 5.0 (+/−0.2) with sulfuric acid and was spray dried to a target moisture of 5%.

In Example 37B, the surface area was reduced. 100 L of bead-milled base silica particle slurry of Example 36A (31% solids) and 380 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 2.3 L/min and 1.0 L/min, respectively, for 165 minutes. After 165 minutes, the flow of sodium silicate was stopped and the pH was reduced to 6.0 (+/−0.2) with continued flow of sulfuric acid at 1.0 L/min. Once the desired pH was reached, the batch was digested for 20 minutes while maintaining pH 6.0 (+/−0.2). The batch was then filtered and washed to a conductivity of <1500 μS. The pH of the surface area reduced silica slurry was then adjusted to 5.0 (+/−0.2) with sulfuric acid and was spray dried to a target moisture of 5%.

For Example 38A, 71.5 L of sodium silicate (2.65 MR, 20.0%), 162 L of deionized water, and 3.6 kg of sodium sulfate were added to a reactor and heated to 85° C. with stirring at 65 RPM and recirculation at 80 L/min. Once 85° C. was reached, sodium silicate (2.65 MR, 20.0%) and sulfuric acid (17.1%) were added simultaneously at 10.9 L/min and 4.6 L/min, respectively, for 47 minutes. After the 47 minutes, the flow of sodium silicate was stopped and the pH was adjusted to pH 6.0 (+/−0.2) with the continued flow of sulfuric acid (17.1%) at 4.6 L/min. The batch was then digested for 15 minutes at 93° C. while maintaining pH 5.8 (+/−0.2). The batch was then de-watered with a filter press and bead milled to a target particle size of 5 μm.

In Example 38B, the surface area was reduced. 100 L of bead-milled base silica particle slurry of Example 38A (31% solids) and 380 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 2.3 L/min and 1.0 L/min, respectively, for 165 minutes. After 165 minutes, the silicate (2.65 MR, 13.3%) and sulfuric acid (11.4%) rates were adjusted to 1.15 L/min and 0.5 L/min, respectively. If needed, the acid rate was adjusted to maintain the batch pH at 9.75 (+/−0.2). After 210 minutes (total), the flow of sodium silicate was stopped and the pH was reduced to 6.0 (+/−0.2) with continued flow of sulfuric acid at 0.5 L/min. Once the desired pH was reached, the batch was digested for 20 minutes while maintaining pH 6.0 (+/−0.2). The batch was then filtered and washed to a conductivity of <1500 μS. The pH of the surface area reduced silica slurry was then adjusted to 5.0 (+/−0.2) with sulfuric acid and was spray dried to a target moisture of 5%.

For Example 39A, 50 L of sodium silicate (2.65 MR, 20.0%) and 162 L of deionized water were added to a reactor and heated to 85° C. with stirring at 60 RPM and recirculation at 80 L/min Once 85° C. was reached, sodium silicate (2.65 MR, 20.0%) and sulfuric acid (17.1%) were added simultaneously at 11.6 L/min and 4.7 L/min, respectively, for 47 minutes. After the 47 minutes, the flow of sodium silicate was stopped and the pH was adjusted to pH 5.8 (+/−0.2) with the continued flow of sulfuric acid (17.1%) at 5.0 L/min. The batch was then digested for 20 minutes at 93° C. while maintaining pH 5.8 (+/−0.2). The batch was then de-watered with a filter press and bead milled to a target particle size of 5 μm.

In Example 39B, the surface area was reduced. 100 L of bead-milled base silica particles slurry of Example 39A (31% solids) and 380 L of water were added to a reactor and heated to 95° C. with stirring at 80 RPM and recirculation at 80 L/min. Once 95° C. was reached, sodium silicate (2.65 MR, 13.3%) was added to bring the pH of the reaction mixture to 9.75 (+/−0.2). Once at the desired pH, sodium silicate (2.65 MR, 13.3%) and sulfuric acid (11.4%) were added at 2.3 L/min and 1.0 L/min, respectively, for 60 minutes. After 60 minutes, the silicate (2.65 MR, 13.3%) and sulfuric acid (11.4%) rates were adjusted to 1.15 L/min and 0.5 L/min, respectively. If needed, the acid rate was adjusted to maintain the batch pH at 9.75 (+/−0.2). After 360 minutes (total), the flow of sodium silicate was stopped and the pH was reduced to 6.0 (+/−0.2) with continued flow of sulfuric acid at 0.5 L/min. Once the desired pH was reached, the batch was digested for 20 minutes while maintaining pH 6.0 (+/−0.2). The batch was then filtered and washed to a conductivity of <1500 μS. The pH of the surface area reduced silica slurry was then adjusted to 5.0 (+/−0.2) with sulfuric acid and was spray dried to a target moisture of 5%.

Figure 9:
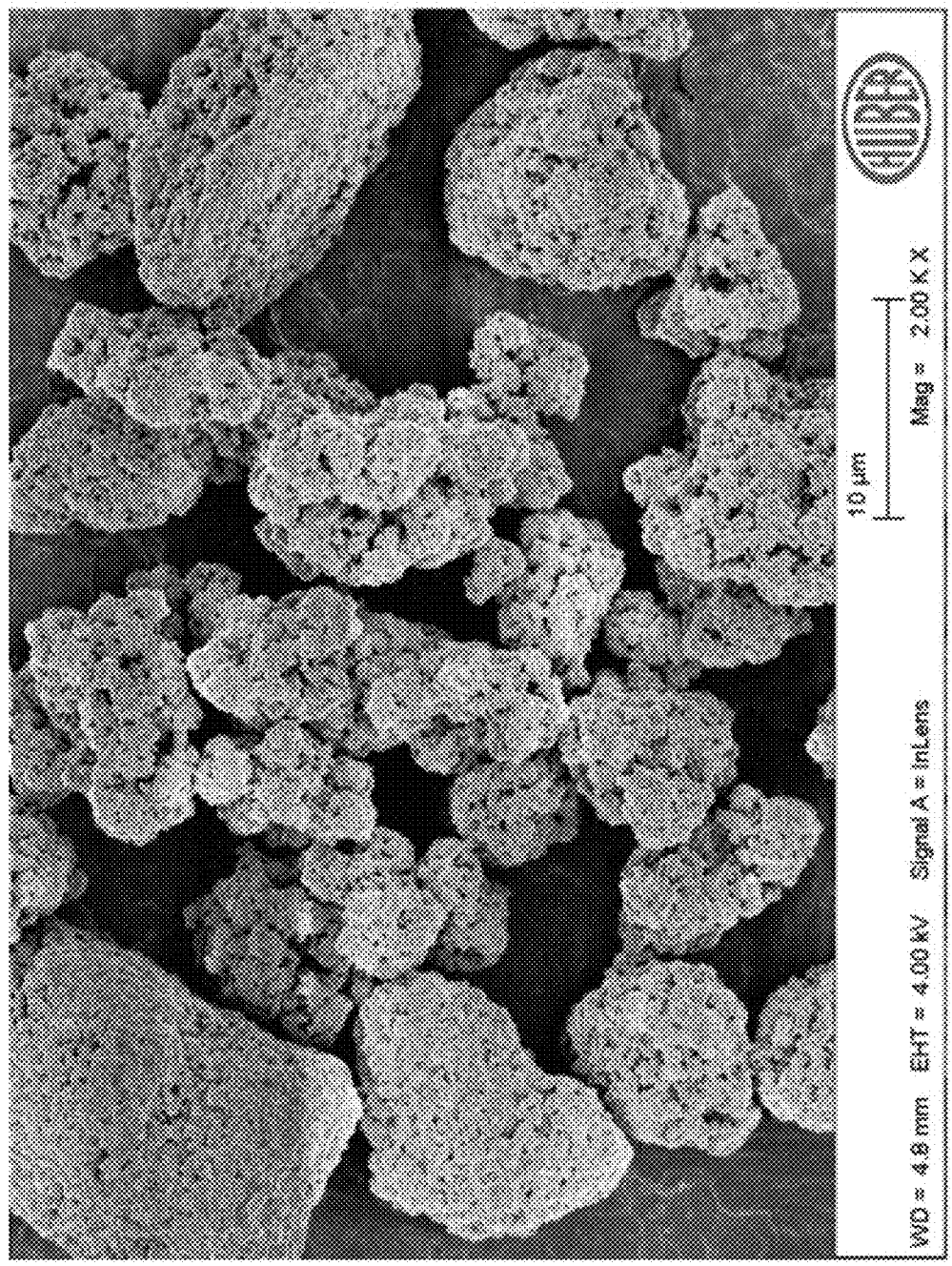
FIGS. 9-10 are Scanning Electron Micrographs of the silica of Example 34B.
Figure 10:
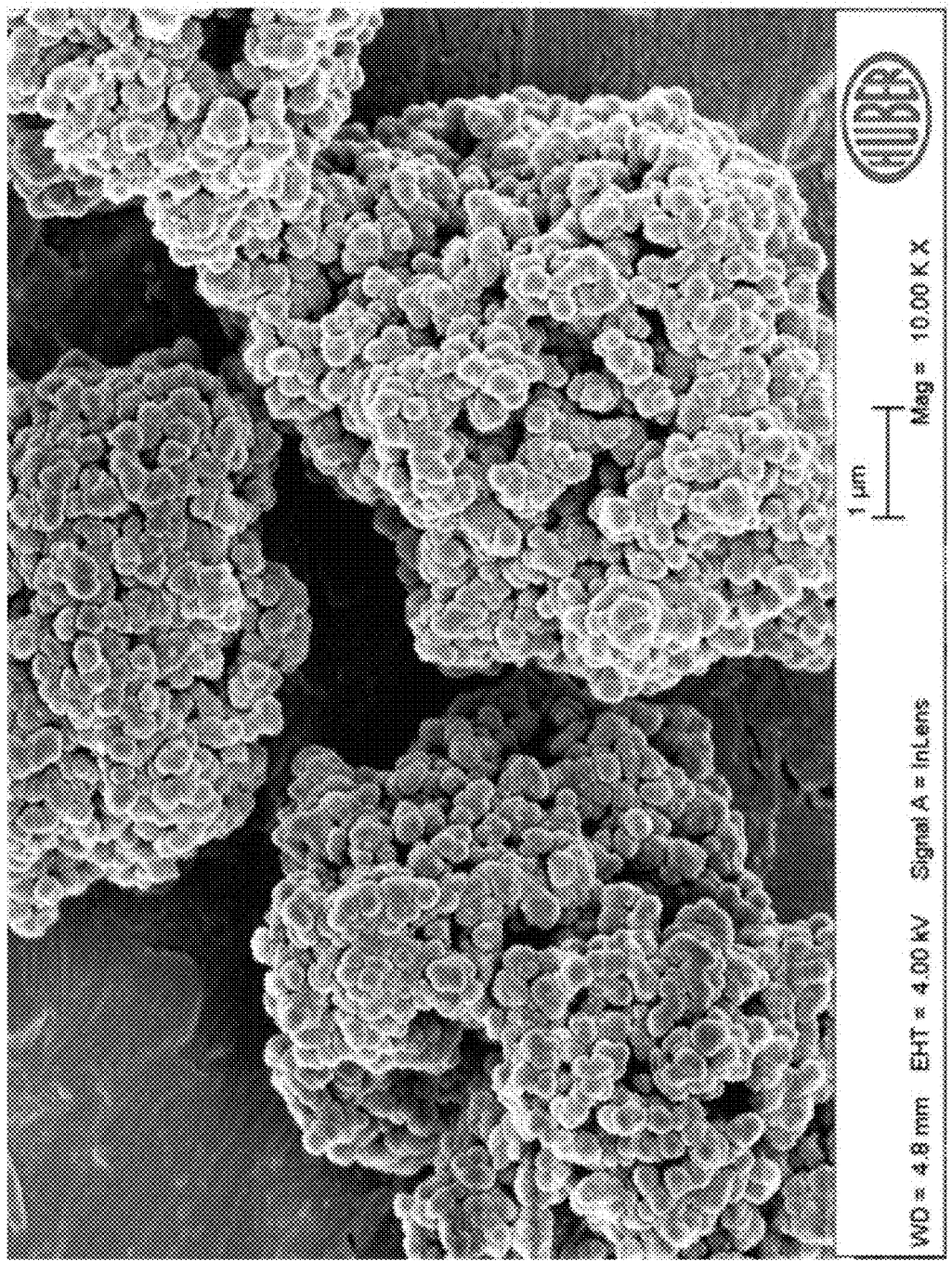
Figure 11:
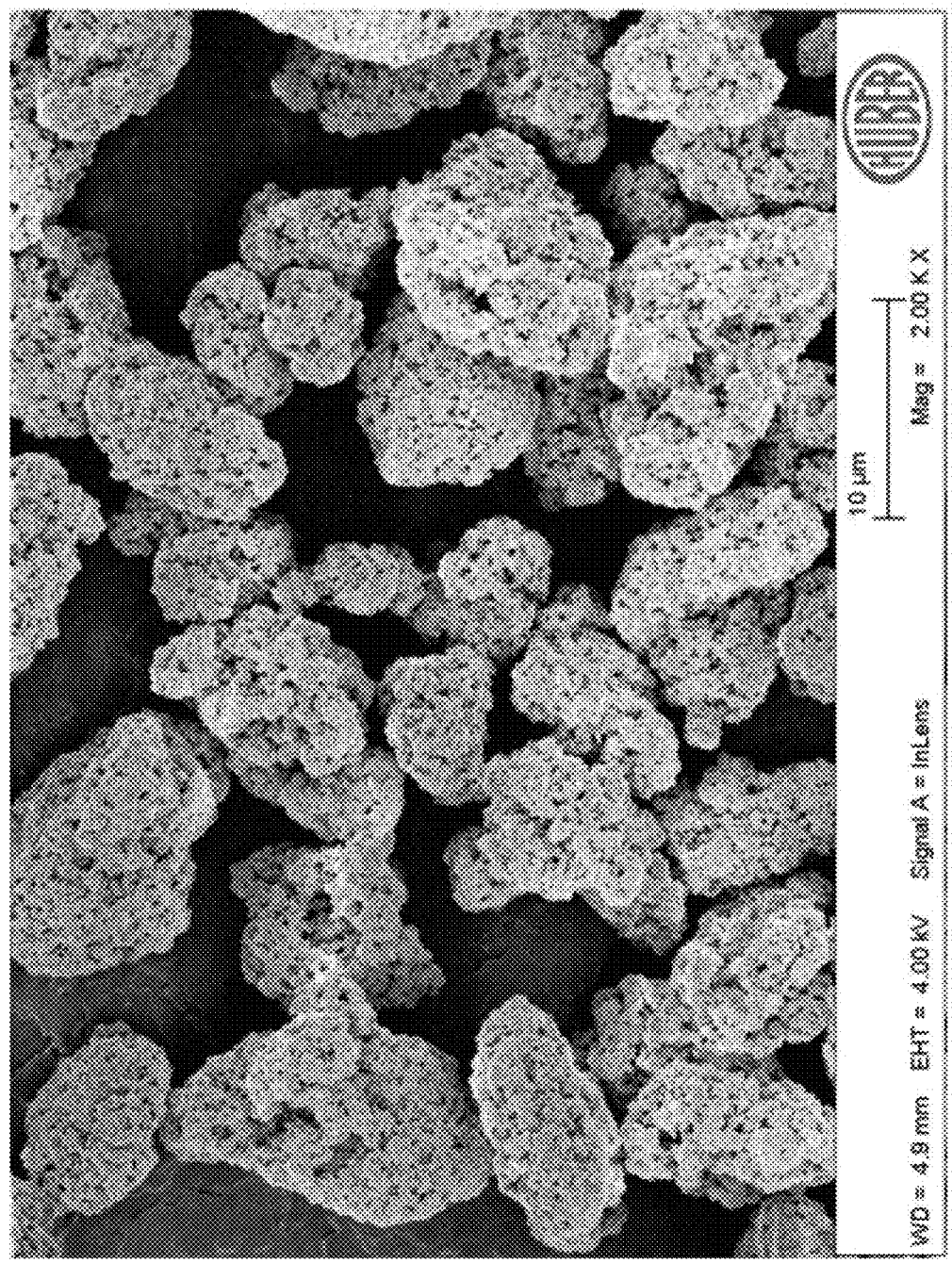
FIGS. 11-12 are Scanning Electron Micrographs of the silica of Example 35B.
Figure 12:
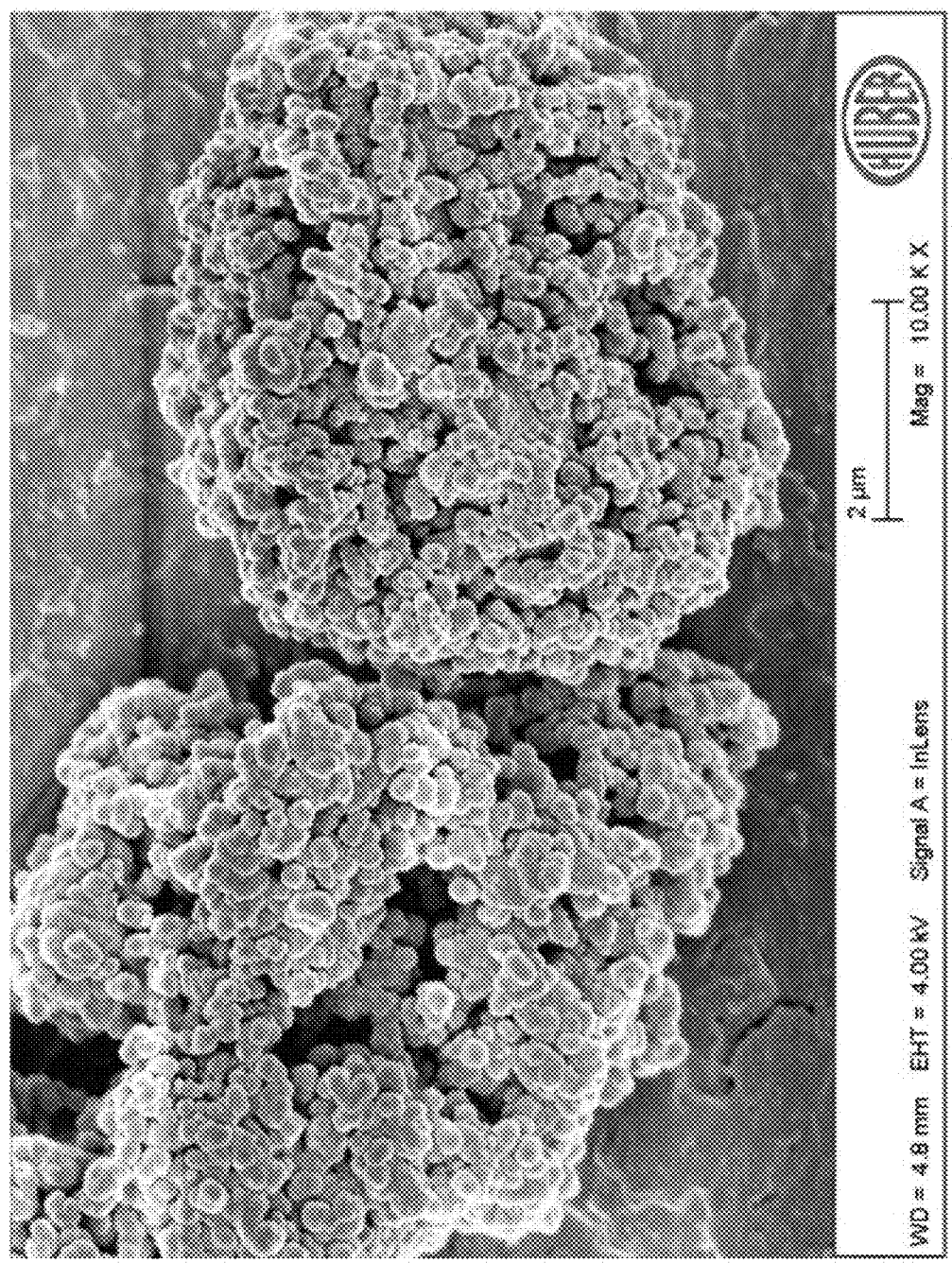

Table VII summarizes certain properties of the silica particles produced in Examples 34-39. Unexpectedly, Examples 34B-35B demonstrated a beneficial combination of BET surface area, pack density, Einlehner abrasion, total mercury intrusion pore volume, stannous compatibility, and/or CPC compatibility. Moreover, these silicas had lower median particles sizes and less than 1% 325 mesh residue. Also, as shown in Table VII, the significant amount of surface area reduction is evident: from 74 to 4 m$^2$/g (Examples 35A-35B). Examination of SEM images for Example 34B (FIGS. 9-10) and Example 35B (FIGS. 11-12) demonstrated a proper open structure and low surface area without over-densification, and with a generally improved particle size distribution for Example 35B over Example 34B.

Figure 13:
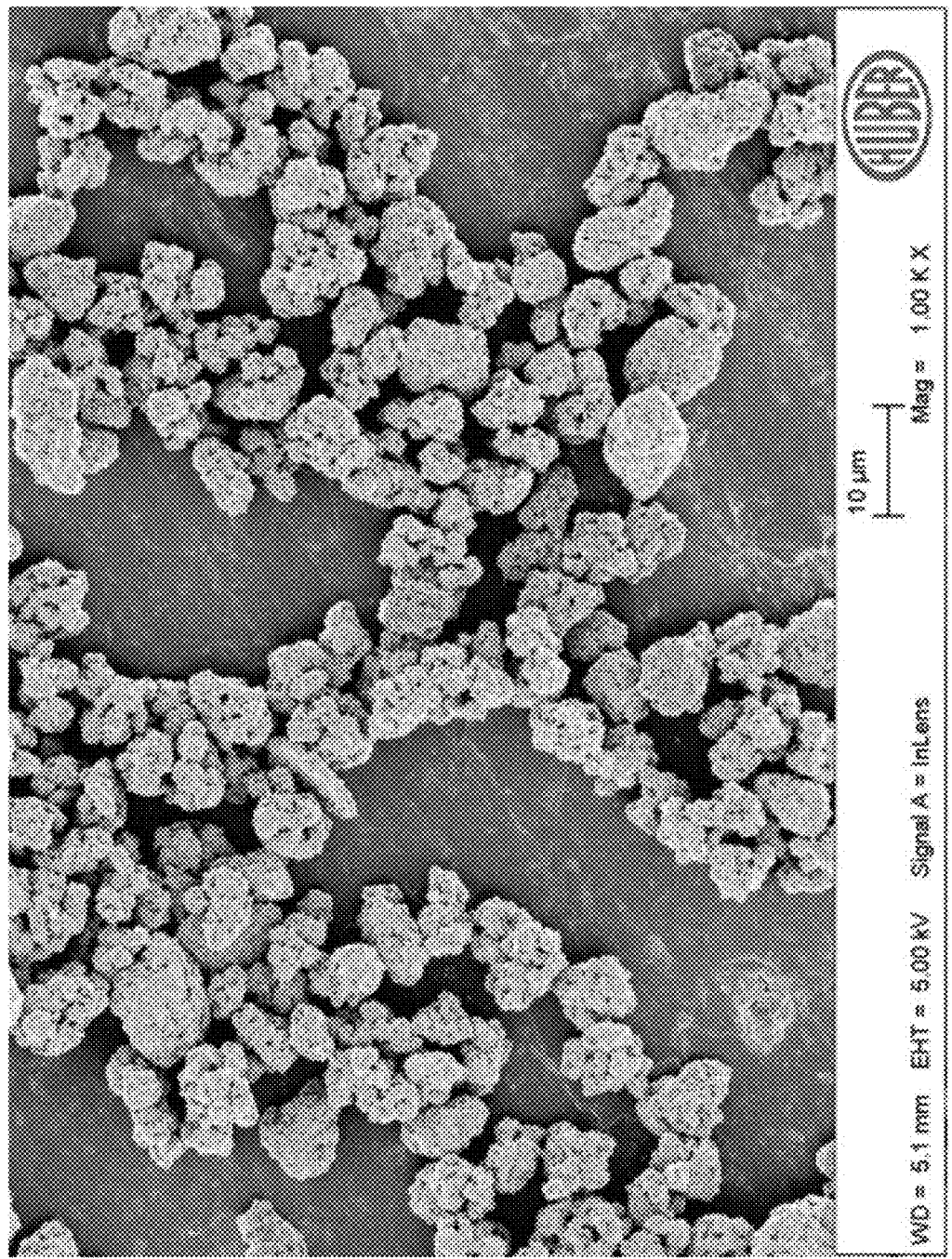
FIGS. 13-14 are Scanning Electron Micrographs of the silica of Example 36B.
Figure 14:
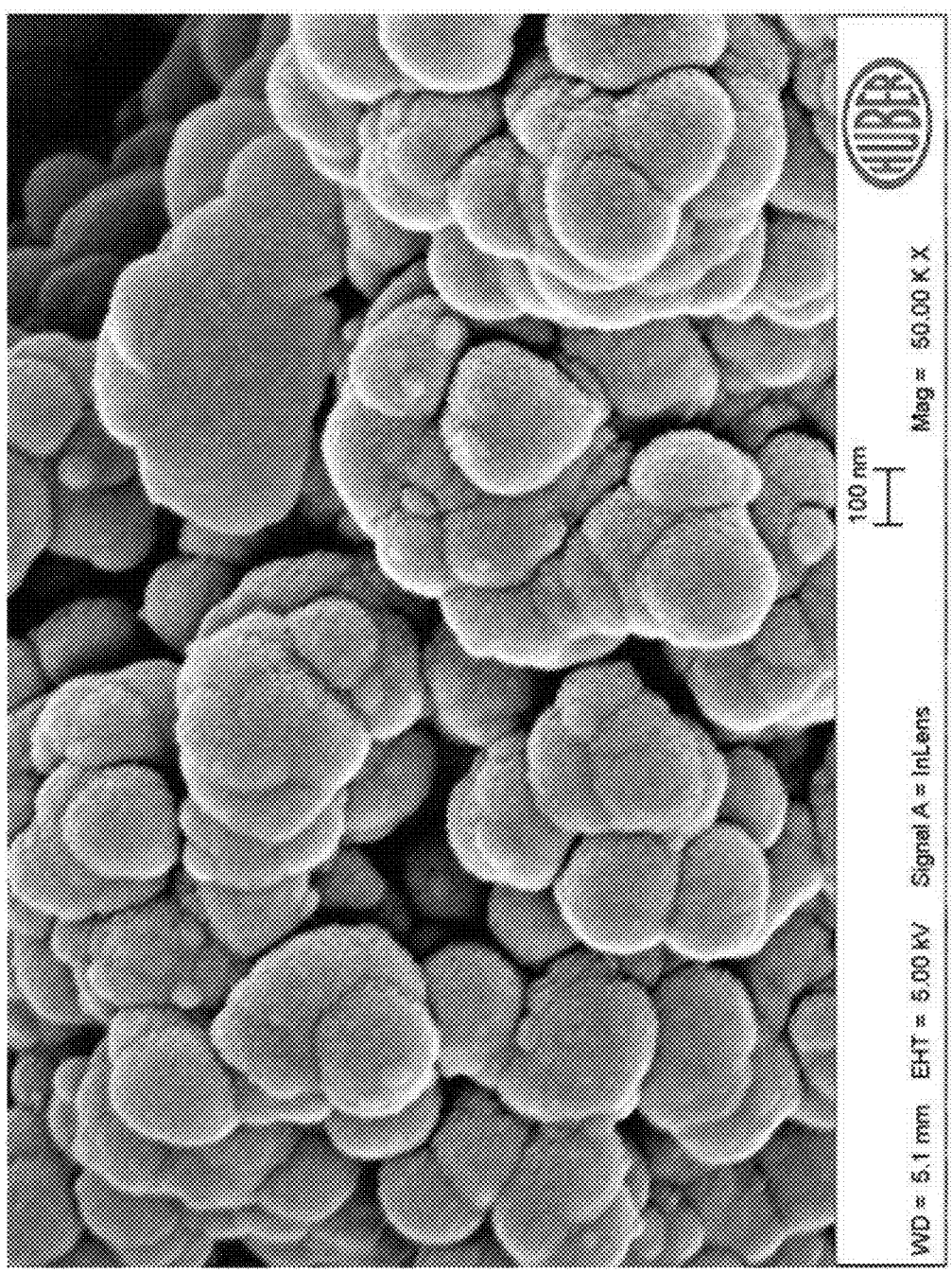

Similar to Examples 34B-35B, Examples 36B-39B demonstrated an unexpected and beneficial combination of BET surface area, pack density, Einlehner abrasion, total mercury intrusion pore volume, stannous compatibility, and/or CPC compatibility, as well as lower median particles sizes and less than 1% 325 mesh residue. Also, as shown in Table VII, the significant amount of surface area reduction is evident: from 31 to 2 $m^2/g$ (Examples 36A-36B) and from 29 to 3 $m^2/g$ (Examples 39A-39B). In the surface area reduction step, the average silica addition rate for Examples 34B-39B ranged from 0.35 to 0.48 wt. % per minute, and the maximum silica addition rate was 0.64 wt. % per minute. Examination of SEM images demonstrated a proper open structure and low surface area without over-densification (e.g., a low pack density), and a narrow particle size distribution. For Examples 36-39, representative SEM images are provided as FIGS. 13-14 (Example 36B).

Table VIII summarizes the RDA, PCR, and the % soluble tin and fluoride after 30 days at 40° C. in dentifrice composition (Example A, an aqueous dentifrice, as described herein) containing the Silica examples. The data in Table VII was collected after the dentifrice was stored for 30 days at a constant temperature of 40° C. After 30 days, the RDA, PCR, soluble tin ion concentration, and soluble fluoride ion concentration were determined by the methods described herein. The % soluble tin after 30 days at 40° C. was determined by dividing the concentration of soluble tin (as measured) by the theoretical concentration of soluble tin (894 ppm) and the % soluble fluoride after 30 days at 40° C. was determined by dividing the concentration of soluble fluoride after 30 days (as measured) by the theoretical soluble fluoride (1100 ppm).

Examples 40-43

Silica Particles Produced with Low BET Surface Areas by the Continuous Loop Reactor Method Examples 40-43 were performed similarly to those of Examples 23-25. For Example 40A, approximately 15 L of previously-made silica slurry at approximately 10% solids was added to the recirculation loop and was circulated at 80 L/min with a high shear Silversion in-line mixer operating at 3600 RPM. The continuous loop reactor was then heated to 65° C. Once 65° C. was reached, sodium silicate (2.55 MR, 13.3%) and sulfuric acid (11.4%) were then continuously added at rates of 2.55 L/min and 1.30 L/min, respectively. If needed, the acid rate was adjusted to maintain a reaction pH of 7.5. 500 L of silica slurry was then collected.

In Example 40B, the surface area was reduced. The silica slurry was heated in a batch reactor to 95° C. with stirring at 80 RPM. Then, 65 L of sodium silicate (2.55 MR, 13.3%) was added to the batch reactor, followed by the simultaneous addition of sodium silicate (2.55 MR, 13.3%) and sulfuric acid (11.4%) at rates of 2.3 L/min and 1.0 L/min, respectively. If needed, the acid rate was adjusted to maintain pH 9.5 (+/−0.2). After 150 minutes from the start of the co-addition of the silicate and acid, the flow of sodium silicate was stopped and the pH was adjusted to 7 with continued addition of sulfuric acid (11.4%) at 0.85 L/min. The batch was digested for 10 minutes at pH 7, and was then filtered and washed to a conductivity of <1500 µS. Prior to drying, the pH of the silica slurry was adjusted to 5 with sulfuric acid and was spray dried to a target moisture of 5%.

For Example 41A, approximately 15 L of previously made silica slurry at approximately 10% solids was added to the recirculation loop and was circulated at 80 L/min with a high shear Silversion in-line mixer operating at 3600 RPM. The continuous loop reactor was then heated to 65° C. Once 65° C. was reached, sodium silicate (2.55 MR, 13.3%) and sulfuric acid (11.4%) were then continuously added at rates of 2.55 L/min and 1.30 L/min, respectively. If needed, the acid rate was adjusted to maintain a reaction pH of 7.5. 500 L of silica slurry was then collected.

In Example 41B, the surface area was reduced. The silica slurry was heated in a batch reactor to 95° C. with stirring at 80 RPM. Then, 65 L of sodium silicate (2.55 MR, 13.3%) was added to the batch reactor, followed by the simultaneous addition of sodium silicate (2.55 MR, 13.3%) and sulfuric acid (11.4%) at rates of 2.3 L/min and 1.0 L/min, respectively. If needed, the acid rate was adjusted to maintain pH 9.5 (+/−0.2). After 165 minutes from the start of the co-addition of the silicate and acid, the flow of sodium silicate was stopped and the pH was adjusted to 7 with continued addition of sulfuric acid (11.4%) at 0.85 L/min. The batch was digested for 10 minutes at pH 7, and was then filtered and washed to a conductivity of <1500 µS. Prior to drying, the pH of the silica slurry was adjusted to 5 with sulfuric acid and was spray dried to a target moisture of 5%.

For Example 42A, approximately 15 L of previously made silica slurry at approximately 10% solids was added to the recirculation loop and was circulated at 80 L/min with a high shear Silversion in-line mixer operating at 3600 RPM. The continuous loop reactor was then heated to 65° C. Once 65° C. was reached, sodium silicate (3.32 MR, 13.0%) and sulfuric acid (11.4%) were then continuously added at rates of 2.55 L/min and 1.07 L/min, respectively. If needed, the acid rate was adjusted to maintain a reaction pH of 7.5. 500 L of silica slurry was then collected.

For Example 42B, the surface area was reduced. The silica slurry was heated in a batch reactor to 95° C. with stirring at 80 RPM. Then, 65 L of sodium silicate (2.55 MR, 13.3%) was added to the batch reactor, followed by the simultaneous addition of sodium silicate (3.32 MR, 13.0%) and sulfuric acid (11.4%) at rates of 2.3 L/min and 0.83 L/min, respectively. If needed, the acid rate was adjusted to maintain pH 9.5 (+/−0.2). After 165 minutes from the start of the co-addition of the silicate and acid, the flow of sodium silicate was stopped and the pH was adjusted to 7 with continued addition of sulfuric acid (11.4%) at 0.83 L/min. The batch was digested for 10 minutes at pH 7, and was then filtered and washed to a conductivity of <1500 µS. Prior to drying, the pH of the silica slurry was adjusted to 5 with sulfuric acid and was spray dried to a target moisture of 5%.

For Example 43A, approximately 15 L of previously made silica slurry at approximately 10% solids was added to the recirculation loop and was circulated at 80 L/min with a high shear Silversion in-line mixer operating at 3600 RPM. The continuous loop reactor was then heated to 65° C. Once 65° C. was reached, sodium silicate (3.32 MR, 13.0%) and sulfuric acid (11.4%) were then continuously added at rates of 2.55 L/min and 1.07 L/min, respectively. If needed, the acid rate was adjusted to maintain a reaction pH of 7.5. 500 L of silica slurry was then collected.

For Example 43B, the surface area was reduced. The silica slurry was heated in a batch reactor to 95° C. with stirring at 80 RPM. Then, 65 L of sodium silicate (2.55 MR, 13.3%) was added to the batch reactor, followed by the simultaneous addition of sodium silicate (3.32 MR, 13.0%)

and sulfuric acid (11.4%) at rates of 2.3 L/min and 0.83 L/min, respectively. If needed, the acid rate was adjusted to maintain pH 9.5 (+/−0.2). After 175 minutes from the start of the co-addition of the silicate and acid, the flow of sodium silicate was stopped and the pH was adjusted to 7 with continued addition of sulfuric acid (11.4%) at 0.83 L/min. The batch was digested for 10 minutes at pH 7, and was then filtered and washed to a conductivity of <1500 μS. Prior to drying, the pH of the silica slurry was adjusted to 5 with sulfuric acid and was spray dried to a target moisture of 5%.

Table IX summarizes certain properties of the silica particles produced in Examples 40-43. As with Examples 23B-25B and Examples 27B-30B, Examples 40B-43B demonstrate an unexpected and beneficial combination of BET surface area, pack density, Einlehner abrasion, stannous compatibility, and pore volume. Due to the loop reactor and surface area reduction processes used to produce the silica particles, it is expected that Examples 40B-43B have both a narrow particle size distribution and spherical particle morphology.

TABLE III

Examples 18-22

| Example | 18B | 19A | 19B | 20B | 21B | 22B |
|---|---|---|---|---|---|---|
| Einlehner (mg lost/100,000 rev) | 11.0 | 4.4 | 10.2 | 9.4 | 12.4 | 12.6 |
| CPC Compatibility (%) | 91 | 0 | 68 | 61 | 89 | 86 |
| Stannous Compatibility (%) | 88 | — | 83 | 78 | 91 | 89 |
| BET Surface Area (m$^2$/g) | 1 | 39 | 6 | 10 | 1 | 2 |
| Total Hg Intrusion Pore Volume (cc/g) | 0.60 | 0.67 | 0.63 | 0.62 | 0.66 | 0.66 |
| CTAB Surface Area (m$^2$/g) | — | 27 | 10 | 10 | 19 | 17 |
| Oil Absorption (cc/100 g) | 33 | 38 | 37 | 36 | 33 | 32 |
| Water AbC (cc/100 g) | 59 | 65 | 66 | 66 | 68 | 77 |
| 5% pH | 6.6 | 6.6 | 6 | 7 | 6.7 | 7.3 |
| Moisture (%) | 3.7 | 5.0 | 5.2 | 4.5 | 4.2 | 5.0 |
| Slurry- Median Particle Size (μm) | — | 5.3 | — | — | — | — |
| Slurry- Mean Particle Size (μm) | — | 5.6 | — | — | — | — |

TABLE I

Examples 1-8

| Example | CPC (%) | Einlehner (mg loss/ 100k rev) | BET (m$^2$/g) | Hg Intrusion Pore Volume (cc/g) | CTAB (m$^2$/g) | Oil (cc/100 g) | Mean (μm) | Median (μm) | 5% pH | 325 Mesh Residue (wt. %) | Sulfate (%) | Pack Density (lb/ft$^3$) |
|---|---|---|---|---|---|---|---|---|---|---|---|---|
| 1 | 65 | 33.8 | 4 | — | 10 | 49 | 20.7 | 13.9 | 7.8 | — | — | — |
| 2 | 82 | 26.8 | 3 | — | 5 | 58 | 8.6 | 6.8 | 7.0 | — | — | — |
| 3 | 55 | 21.8 | 3 | — | 6 | 69 | — | 7.7 | 8.2 | — | — | — |
| 4 | 67 | 12.6 | 2 | 1.26 | 3 | 78 | — | 5.9 | 6.8 | 0.2 | — | — |
| 5 | 96 | 21.4 | 2 | 0.83 | — | 44 | 7.2 | 6.8 | 7.2 | 1.2 | 0.59 | 59.5 |
| 6 | 90 | 22.4 | 1 | 0.82 | — | 39 | 7.8 | 7.3 | 7.1 | 0.4 | 0.35 | 73.4 |
| 7 | 90 | 18.6 | 3 | 0.79 | — | 46 | 6.3 | 5.7 | 7.3 | 1.1 | 0.35 | 56.8 |
| 8 | 92 | 20.3 | 1 | 0.81 | — | 40 | 8.0 | 7.5 | 5.9 | 0.4 | 0.43 | 59.5 |

TABLE II

Examples 9-17

| Example | 9 | 10 | 11 | 12 | 13 | 14 | 15 | 16 | 17 |
|---|---|---|---|---|---|---|---|---|---|
| Einlehner (mg lost/100,000 rev) | 44.0 | 36.0 | 38.0 | 29.2 | 34.1 | 27.7 | 31.6 | 35.2 | 26.9 |
| CPC Compatibility | 91 | 89 | 90 | 83 | 83 | 76 | 69 | 91 | 75 |
| Stannous Compatibility (%) | 92 | 80 | 84 | 71 | 74 | 59 | 47 | 93 | 58 |
| BET Surface Area (m$^2$/g) | 1 | 1 | 4 | 3 | 4 | 5 | 15 | 11 | 8 |
| Total Hg Intrusion Pore Volume (cc/g) | 0.69 | 0.74 | 0.62 | 0.81 | 0.76 | 0.71 | 0.77 | 0.53 | 0.78 |
| CTAB Surface Area (m$^2$/g) | 3 | 8 | 9 | 9 | 8 | 9 | 12 | 7 | 8 |
| Oil Absorption (cc/100 g) | 43 | 48 | 44 | 40 | 42 | 28 | 32 | 45 | 61 |
| Water AbC (cc/100 g) | 74 | 74 | 71 | 87 | 80 | 78 | 77 | 67 | 74 |
| 5% pH | 8.9 | 8 | 8.3 | 8.1 | 8.2 | 7.7 | 8.1 | 6.2 | 6.2 |
| Moisture (%) | 4.2 | 4.2 | 3.8 | 4.9 | 4.1 | 4.2 | 4.2 | 3.3 | 4.4 |
| Median Particle Size (μm) | 13.2 | 12.7 | 10.8 | 9.3 | 9.9 | 9 | 9.3 | 11.1 | 8.7 |
| Mean Particle Size (μm) | 13.7 | 11.8 | 19.3 | 15.7 | 12.8 | 11.4 | 11.3 | 15.9 | 14.2 |
| 325 Mesh Residue (wt. %) | 5.1 | 16.1 | 12.9 | 4.7 | 12.7 | 5.5 | 8.3 | 7.6 | 12.6 |
| Sodium Sulfate (%) | <0.35 | <0.35 | <0.35 | <0.35 | <0.35 | <0.35 | <0.35 | <0.35 | <0.35 |
| Pour Density (lb/ft$^3$) | 41.6 | 37.8 | 38.2 | 38.2 | 33.4 | 36 | 39.8 | 36.7 | 33.3 |
| Pack Density (lb/ft$^3$) | 62.4 | 58.5 | 62.4 | 55.1 | 56.8 | 56.8 | 56.8 | 63.2 | 57.4 |

TABLE III-continued

Examples 18-22

| Example | 18B | 19A | 19B | 20B | 21B | 22B |
|---|---|---|---|---|---|---|
| Slurry- d95 (μm) | — | 11.0 | — | — | — | — |
| Median Particle Size (μm) | 6.5 | — | 6.4 | 7.0 | 7.1 | 9.5 |
| Mean Particle Size (μm) | 6.8 | — | 6.5 | 7.1 | 7.1 | 9.6 |
| 325 Mesh Residue (wt. %) | 0.5 | 0.3 | 0.1 | 0.1 | 0.1 | 0.4 |
| Sodium Sulfate (%) | 1.14 | 2.4 | 0.9 | 1.6 | 2.5 | 1.2 |
| Pour Density (lb/ft$^3$) | 41.2 | 35.7 | 39.0 | 40.3 | 39.0 | 37.8 |
| Pack Density (lb/ft$^3$) | 60.0 | 54.3 | 59.5 | 59.5 | 58.1 | 56.8 |
| Average silica addition rate (%/min) | 0.68 | — | 0.48 | 0.65 | 0.60 | 0.67 |
| Maximum silica addition rate (%/min) | 0.92 | — | 0.50 | 0.92 | 0.92 | 0.92 |

TABLE IV

Examples 23-25

| Example | 23A | 23B | 24A | 24B | 25B |
|---|---|---|---|---|---|
| Einlehner (mg lost/100,000 rev) | 7.5 | 19.5 | — | 19.4 | 17.9 |
| CPC Compatibility (%) | 0 | 96 | — | 93 | 95 |
| Stannous Compatibility (%) | 6 | 93 | — | 89 | 93 |
| BET Surface Area (m$^2$/g) | 302 | 0.6 | 280 | 1.3 | 0.7 |
| Total Hg Intrusion Pore Volume (cc/g) | 1.31 | 0.82 | 0.93 | 0.89 | 0.81 |
| CTAB Surface Area (m$^2$/g) | 112 | 3 | 98 | 4 | 3 |
| Oil Absorption (cc/100 g) | 89 | 43 | n/a | 39 | 39 |
| Water AbC (cc/100 g) | 105 | 84 | 91 | 81 | 77 |
| 5% pH | 7.1 | 6.5 | 7.3 | 6.4 | 6.5 |
| Moisture (%) | 7.5 | 4.5 | 5.3 | 3.5 | 3.5 |
| Slurry- Median Particle Size (μm) | 5.8 | — | 5.5 | — | — |
| Slurry- Mean Particle Size (μm) | 6.2 | — | 5.9 | — | — |
| Slurry- d95 (μm) | 12.2 | — | 11.0 | — | — |
| Median Particle Size (μm) | — | 8.5 | — | 7.0 | 6.6 |
| Mean Particle Size (μm) | — | 8.5 | — | 7.1 | 6.7 |
| 325 Mesh Residue (wt. %) | 1.9 | 0.3 | 0.0 | 0.1 | 0.1 |
| Sodium Sulfate (%) | 2.0 | 1.8 | — | 1.6 | 1.7 |
| Pour Density (lb/ft$^3$) | 23.1 | 34.7 | 22.3 | 32 | 34.7 |
| Pack Density (lb/ft$^3$) | 36.7 | 54.3 | 37.8 | 49.9 | 54.3 |
| Average silica addition rate (%/min) | — | 0.66 | — | 0.47 | 0.36 |
| Maximum silica addition rate (%/min) | — | 0.92 | — | 0.92 | 0.50 |

TABLE V

Examples 26-30

| Example | 26A | 26B | 27B | 28B | 29B | 30B |
|---|---|---|---|---|---|---|
| Einlehner (mg lost/100,000 rev) | 2.2 | 14.6 | 16.1 | 14.5 | 16.3 | 14.4 |
| CPC Compatibility (%) | — | 54 | 88 | 82 | 81 | 76 |
| Stannous Compatibility (%) | 6 | 67 | 83 | 83 | 82 | 84 |
| BET Surface Area (m$^2$/g) | 232 | 7.7 | 1.6 | 2.3 | 2.8 | 3.2 |
| Total Hg Intrusion Pore Volume (cc/g) | 2.21 | 0.91 | 0.75 | 0.79 | 0.80 | 0.78 |
| CTAB Surface Area (m$^2$/g) | 113 | 4 | 0 | 0 | 0 | 1 |
| Oil Absorption (cc/100 g) | 102 | 56 | 42 | 42 | 44 | 30 |
| Water AbC (cc/100 g) | 125 | 86 | 80 | 80 | 82 | 81 |
| 5% pH | 7.3 | 7.1 | 7.1 | 7.0 | 7.0 | 6.7 |
| Moisture (%) | 6.8 | 4.6 | 4.1 | 4.5 | 4.9 | 4.6 |
| Slurry- Median Particle Size (μm) | 5.2 | — | — | — | — | — |
| Slurry- Mean Particle Size (μm) | 5.2 | — | — | — | — | — |
| Slurry- d95 (μm) | 10.2 | — | — | — | — | — |
| Median Particle Size (μm) | — | 6.0 | 6.2 | 6.0 | 6.0 | 6.0 |
| Mean Particle Size (μm) | — | 6.3 | 6.4 | 6.2 | 6.2 | 6.2 |
| 325 Mesh Residue (wt. %) | 3.5 | 0.3 | 0.1 | 0.0 | 0.1 | 0.1 |
| Sodium Sulfate (%) | 1.45 | 1.45 | 1.69 | 1.69 | 1.61 | 1.84 |
| Pour Density (lb/ft$^3$) | 18.4 | 31.2 | 33.4 | 37.5 | 36.0 | 36.0 |
| Pack Density (lb/ft$^3$) | 30.2 | 49.3 | 52.0 | 52.0 | 49.3 | 49.3 |
| Average silica addition rate (%/min) | — | 0.66 | 0.37 | 0.37 | 0.37 | 0.38 |
| Maximum silica addition rate (%/min) | — | 0.92 | 0.50 | 0.50 | 0.50 | 0.50 |

TABLE VI

Examples 31-33

| Example | 31B | 32A | 32B | 33A | 33B |
|---|---|---|---|---|---|
| Einlehner (mg lost/100k rev) | 17.7 | 12.0 | 11.3 | 5.0 | 29.0 |
| CPC Compatibility (%) | 76 | 0 | 43 | 0 | 85 |
| Stannous Compatibility (%) | 78 | 25 | 58 | 22 | 99 |
| BET Surface Area (m$^2$/g) | 3 | 40 | 11 | 88 | 2 |
| Total Hg Intrusion Pore Volume (cc/g) | 0.86 | 1.13 | 1.20 | 1.57 | 0.77 |
| CTAB Surface Area (m$^2$/g) | 38 | 13 | 29 | 2 | 1 |
| Oil Absorption (cc/100 g) | 30 | 102 | 79 | 80 | 58 |
| Water AbC (cc/100 g) | 86 | 79 | 119 | 109 | 80 |
| 5% pH | 6.3 | 7.5 | 6.4 | 7.2 | 6.5 |
| Moisture (%) | 3.6 | 6.4 | 4.4 | 6.9 | 2.7 |
| Slurry- Median Particle Size (μm) | — | 5.4 | — | 7.3 | — |
| Slurry- Mean Particle Size (μm) | — | 6.2 | — | 8.1 | — |
| Slurry- d95 (μm) | — | — | — | 14.2 | — |
| Median Particle Size (μm) | 10.8 | — | 10.0 | — | 10.9 |
| Mean Particle Size (μm) | 11.0 | — | 10.1 | — | 10.6 |
| 325 Mesh Residue (wt. %) | 0.1 | 1.46 | 2.03 | 1.24 | 0.93 |
| Sodium Sulfate (%) | <0.35 | 4.12 | 0.51 | 9.4 | <0.35 |
| Pour Density (lb/ft$^3$) | 44.6 | 24.0 | 27.1 | 18.6 | 39 |
| Pack Density (lb/ft$^3$) | 65.0 | 49.9 | 40.3 | 32.9 | 56.8 |
| Average silica addition rate (%/min) | 0.97 | — | 0.97 | — | 0.92 |
| Maximum silica addition rate (%/min) | 2.62 | — | 2.46 | — | 2.62 |

TABLE VII

Examples 34-39

| Example | 34A | 34B | 35A | 35B | 36A | 36B | 37B | 38A | 38B | 39A | 39B |
|---|---|---|---|---|---|---|---|---|---|---|---|
| Einlehner (mg lost/100k rev) | 9.4 | 20.2 | 13.7 | 18.9 | 7.9 | 19.6 | 17.6 | 7.8 | 20.7 | 2.9 | 21.2 |
| CPC Compatibility (%) | 0 | 80 | 0 | 73 | 0 | 84 | 70 | 0 | 80 | — | 80 |

TABLE VII-continued

Examples 34-39

| Example | 34A | 34B | 35A | 35B | 36A | 36B | 37B | 38A | 38B | 39A | 39B |
|---|---|---|---|---|---|---|---|---|---|---|---|
| Stannous Compatibility (%) | 25 | 87 | 25 | 83 | 19 | 89 | 78 | 30 | 84 | 24 | 84 |
| BET Surface Area (m²/g) | 35 | 3 | 74 | 4 | 31 | 2 | 5 | 26 | 3 | 29 | 3 |
| Total Hg Intrusion Pore Volume (cc/g) | 1.35 | 1.08 | 1.20 | 0.98 | 1.40 | 0.98 | 1.08 | 1.40 | 1.05 | 1.46 | 0.95 |
| CTAB Surface Area (m²/g) | 26 | 2 | 20 | 1 | 33 | 5 | 7 | 26 | 5 | 32 | 5 |
| Oil Absorption (cc/100 g) | 99 | 59 | 69 | 55 | 74 | 40 | 60 | 74 | 42 | 80 | 40 |
| Water AbC (cc/100 g) | 91 | 102 | 76 | 99 | 105 | 94 | 105 | 102 | 108 | 103 | 97 |
| 5% pH | 7.2 | 6.7 | 7.2 | 6.7 | 7.0 | 7.3 | 6.9 | 7.2 | 8.4 | 6.9 | 8.6 |
| Moisture (%) | 5.7 | 2.7 | 5 | 3.2 | 6.5 | 4.5 | 4.9 | 6.2 | 4.3 | 6.8 | 4.6 |
| Slurry- Median Particle Size (μm) | 5.1 | — | 4.7 | — | 5.0 | — | — | 5.4 | — | 5.3 | — |
| Slurry- Mean Particle Size (μm) | 5.6 | — | 5.1 | — | 5.6 | — | — | 5.9 | — | 6.2 | — |
| Slurry- d95 (μm) | 11.3 | — | 10.2 | — | 11.2 | — | — | 11.2 | — | 13.0 | — |
| Median Particle Size (μm) | — | 7.4 | — | 7.5 | — | 6.9 | 6.6 | — | 6.9 | — | 7.4 |
| Mean Particle Size (μm) | — | 7.7 | — | 7.8 | — | 7.1 | 7.0 | — | 7.2 | — | 6.8 |
| 325 Mesh Residue (wt. %) | 0.83 | 0.81 | 1.32 | 0.49 | 0.65 | 0.49 | 0.87 | 0.20 | 0.30 | 0.14 | 0.30 |
| Sodium Sulfate | 7.6 | 7.6 | 5.54 | <0.35 | — | <0.35 | <0.35 | — | <0.35 | — | <0.35 |
| Pour Density (lb/ft³) | 21.5 | 30.5 | 24.5 | 28.4 | 22.3 | 31.2 | 28.4 | 23.4 | 32.3 | 20.8 | 29.3 |
| Pack Density (lb/ft³) | 36.7 | 46.2 | 46.2 | 46.2 | 34.7 | 46.8 | 40.7 | 34.7 | 46.2 | 33.4 | 46.8 |
| Average silica addition rate (%/min) | — | 0.40 | — | 0.44 | — | 0.44 | 0.48 | — | 0.35 | — | 0.32 |
| Maximum silica addition rate (%/min) | — | 0.64 | — | 0.64 | — | 0.64 | 0.64 | — | 0.64 | — | 0.64 |

TABLE VIII

| Dentifrice Composition containing Example | RDA | PCR | % Extractable Stannous Ion Concentration in Full Composition after 30 days at 40° C. | % Soluble Fluoride after 30 days at 40° C. |
|---|---|---|---|---|
| 9 | 228 | 103 | 91% | 83% |
| 10 | 192 | 100 | 91% | 83% |
| 11 | 220 | 147 | 81% | 78% |
| 12 | 176 | 116 | 63% | 80% |
| 13 | 203 | 141 | 69% | 76% |
| 14 | 193 | 140 | 51% | 76% |
| 15 | 191 | 140 | 47% | 81% |
| 16 | 216 | 130 | 94% | 82% |
| 17 | 195 | 130 | 54% | 76% |
| 18B | 173 | 127 | 93% | 86% |
| 19A | N/A | N/A | N/A | N/A |
| 19B | 257 | 113 | 87% | 83% |
| 20B | 238 | 118 | 89% | 81% |
| 21B | 238 | 110 | 100% | 76% |
| 22B | 241 | 102 | 98% | 77% |
| 23A | 150 | 77 | 28% | 89% |
| 23B | 186 | 116 | 100% | 79% |
| 24A | 148 | 97 | 25% | 86% |
| 24B | 176 | 113 | 100% | 79% |
| 25B | 204* | 102 | 100% | 80% |
| 26A | 134 | 85 | 21% | 81% |
| 26B | 166 | 106 | 69% | 77% |
| 27B | 166 | 109 | 90% | 74% |
| 28B | 169 | 118 | 83% | 75% |
| 29B | 177 | 102 | 74% | 75% |
| 30B | 179 | 118 | 80% | 74% |
| 31 | 171* | 122 | 90% | 84% |
| 32A | 146 | 92 | 34% | 83% |
| 32B | N/A | N/A | N/A | N/A |
| 33A | 72 | 55 | 34% | 86% |
| 33B | 188* | 132 | 96% | 84% |
| 34A | 96 | 90 | 31% | 87% |
| 34B | 178* | 157* | 93% | 88% |
| 35A | 146 | 116 | 33% | 84% |

TABLE VIII-continued

| Dentifrice Composition containing Example | RDA | PCR | % Extractable Stannous Ion Concentration in Full Composition after 30 days at 40° C. | % Soluble Fluoride after 30 days at 40° C. |
|---|---|---|---|---|
| 35B | 163* | 121 | 98% | 88% |
| 36A | 96 | 84 | 37% | 83% |
| 36B | 190 | 135* | 94% | 82% |
| 37B | 192 | 124* | 94% | 84% |
| 38A | 103 | 83 | 34% | 82% |
| 38B | 190 | 149* | 100% | 82% |
| 39A | 36 | 45 | 30% | 80% |
| 39B | 172 | 143 | 97% | 83% |

*2-4 measurements were taken and the mean was calculated.

TABLE IX

Examples 41-43

| Example | 40B | 41B | 42B | 43B |
|---|---|---|---|---|
| Einlehner (mg lost/100k rev) | 10.9 | 13.5 | 14.1 | 15.9 |
| Stannous Compatibility (%) | 73 | 77 | 73 | 76 |
| BET Surface Area (m$^2$/g) | 6 | 5 | 7 | 5 |
| Total Hg Intrusion Pore Volume (cc/g) | 0.93 | 0.94 | 1.04 | 1.00 |
| CTAB Surface Area (m$^2$/g) | 5 | 7 | — | — |
| Oil Absorption (cc/100 g) | 69 | 71 | 66 | 79 |
| Water AbC (cc/100 g) | 91 | 94 | 88 | 96 |
| 5% pH | 7.5 | 6.7 | 7.0 | 7.0 |
| Moisture (%) | 2.6 | 3.2 | 2.5 | 2.6 |
| Median Particle Size (μm) | 4.8 | 6.1 | 6.5 | 6.6 |
| Mean Particle Size (μm) | 5.0 | 6.2 | 6.6 | 6.7 |
| Sodium Sulfate (%) | 0.82 | 1.61 | 1.45 | 1.45 |
| Pour Density (lb/ft$^3$) | 32.3 | 31.2 | 30.5 | 30.5 |
| Pack Density (lb/ft$^3$) | 46.0 | 44.6 | 46.2 | 46.2 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Combinations

A. A dentifrice composition comprising: (a) an abrasive comprising precipitated silica particles; (b) a stannous ion source wherein the extractable stannous ions after 30 days at 40° C. is greater than about 75% of the initial extractable stannous ion concentration.

B. A dentifrice composition comprising: (a) an abrasive comprising precipitated silica particles; (b) a stannous ion source wherein the extractable stannous ions after 30 days at 40° C. is greater than about 65% of the initial extractable stannous ion concentration; (c) a fluoride ion source wherein the percent soluble fluoride after 30 days at 40° C. is greater than about 75% of the initial fluoride concentration; wherein the average RDA is less than about 220.

C. A dentifrice composition comprising: (a) an abrasive comprising precipitated silica particles wherein the precipitated silica particles have a total mercury intrusion from 0.7 to about 1.2 cc/g; (b) a stannous ion source wherein the composition wherein an extractable stannous ions after 30 days at 40° C. is greater than about 80% of the initial extractable stannous ion concentration; (c) a soluble fluoride ion source wherein the composition comprises from about 550 ppm to about 1100 ppm soluble fluoride ions; wherein the dentifrice composition has an average RDA less than about 250; wherein the dentifrice composition has an average PCR greater than about 90.

D. The dentifrice of paragraphs A-C wherein the composition has an average RDA from about 70 to about 250; in another example from about 70 to about 225; in another example from about 70 to about 200; in another example from about 90 to about 200; and in another example from about 110 to about 200.

E. The dentifrice composition of paragraphs A-D wherein the average RDA is less than about 250; in another example less than about 225; in another example less than about 210; and in another example less than 200.

F. The dentifrice composition of paragraphs A-E wherein the extractable stannous ion concentration greater than about 500 ppm stannous ions; in another example greater than greater than about 600 ppm; in another example greater than about 800 ppm; in another example greater than about 1000 ppm, greater than about 1200 ppm; in another example greater than about 1500 ppm; in another example greater than about 2500 ppm; and in another example greater than about 3000 ppm.

G. The dentifrice composition of paragraphs A-F wherein the extractable stannous ion concentration is from about 500 ppm to about 4000 ppm; in another example from about 600 ppm to about 3500 ppm; in another example from about 700 ppm to about 3000 ppm; in another example from about 900 ppm to about 2500 ppm; and in another example from about 1000 ppm to about 2000 ppm.

H. The dentifrice composition of paragraphs A-G wherein the composition has an average PCR from about 60 to about 200; in another example from about 70 to about 170; in another example from about 80 to about 160; in another example from about 90 to about 150; and in another example from about 100 to about 140.

I. The dentifrice composition of paragraphs A-H wherein the average PCR is greater than about 80; in another example greater than about 100; in another example greater than about 110; in another example greater than about 120; and in another example greater than about 130.

J. The dentifrice composition of paragraphs A-I wherein the precipitated silica particles have a total mercury intrusion from 0.6 to 1.5 cc/g; in another example from about 0.9 to about 1.1 cc/g; in another example from about 0.7 to about 1.2 cc/g; in another example from about 0.75 to about 0.9 cc/g; and in another example from about 0.9 to about 1.1 cc/g.

K. The dentifrice composition of paragraphs A-J wherein the extractable stannous ions after 30 days at 40° C. is greater than about 65%; in another example greater than about 75%; in another example greater than about 80%; in another example greater than about 85%; in another example greater than about 90%; in another example greater than about 93%; and in another example greater than about 90%.

L. The dentifrice composition of paragraphs A-K wherein the extractable stannous ions after 30 days at 40° C. is from about 55% to 100%; in another example from 63% to 100%; in another example from 72% to 100%; in another example from 83% to 100%; in another example from 91% to 99%; and in another example from 95% to 99%.

M. The dentifrice composition of paragraphs A-L further comprising an antimicrobial agent selected from the group consisting of zinc citrate, zinc lactate, and combinations thereof, wherein the dentifrice composition comprises from about 900 ppm to 1750 ppm soluble zinc ions; in another example from about 1000 ppm to about 1600 ppm; in another example from about 1200 ppm to about 1500 ppm; and in another example from about 1300 ppm to about 1400 ppm.

N. The dentifrice composition of paragraphs A-M further comprising an antimicrobial agent selected from the group consisting of zinc citrate, zinc lactate, and combinations thereof, wherein the dentifrice composition comprises from about 300 ppm to about 650 pm; in another example from about 400 ppm to about 600 ppm; and in another example from about 450 ppm to about 550 ppm.

O. The dentifrice composition of paragraphs A-N wherein the dentifrice comprises from about 1% to about 60% abrasive; in another example from about 5% to about 45%; and in another example from about 7% to about 27% abrasive.

P. The dentifrice composition of paragraphs A-O wherein the precipitated silica particles have a BET surface area in a range from about 0.1 to about 7 $m^2/g$; in another example from about 0.5 to about 3.5 $m^2/g$; and in another example from about 1.5 to about 7 $m^2/g$.

Q. The dentifrice composition of paragraphs A-P wherein the silica particles comprise an Einlehner abrasion value from about 8 to about 25 mg lost/100,000 revolutions; in another example from about 10 to about 20 mg lost/100,000 revolutions; and in another example from about 15 to about 22 mg lost/100,000 revolutions.

R. The dentifrice composition of paragraphs A-Q wherein the stannous ion source is selected from the group consisting of stannous fluoride, stannous chloride dihydrate, stannous acetate, stannous gluconate, stannous oxalate, stannous sulfate, stannous lactate, and stannous tartrate.

S. The dentifrice composition of paragraph R wherein the stannous ion source is stannous fluoride.

T. The dentifrice composition of paragraph R wherein the stannous ion source is stannous chloride dihydrate.

U. The dentifrice composition of paragraphs A-T wherein the silica particles comprise a pack density from about 30 to about 60 $lb/ft^3$; in another example from about 35 to about 55 $lb/ft^3$; in another example from about 45 to about 55 $lb/ft^3$; and in another example from about 40 to about 50 $lb/ft^3$.

V. The dentifrice composition of paragraphs A-U wherein the silica particles comprise a CPC compatibility from about 70 to about 99%.

W. The dentifrice composition of paragraphs A-V further comprising a flavor.

X. The dentifrice composition of paragraphs A-W further comprising a thickening agent selected from the group consisting of carboxyvinyl polymers, carrageenan, hydroxyethyl cellulose, sodium carboxymethylcellulose sodium hydroxyethyl cellulose, gum karaya, xanthan gum, gum arabic, gum tragacanth, and combinations thereof.

Y. The dentifrice composition of paragraphs A-X further comprising from about 10% to about 70% of a humectant; in another example from about 15% to about 60%; in another example from about 20% to about 60%; wherein the humectant is selected from the group consisting of glycerin, sorbitol, polyethylene glycol, propylene glycol, xylitol, and combinations thereof.

Z. The dentifrice composition of paragraphs A-Y further comprising a surfactant selected from the group consisting of anionic, nonionic, amphoteric, zwitteronic, cationic, and combinations thereof.

AA. The dentifrice composition of paragraph Z wherein the surfactant is an anionic surfactant and wherein the anionic surfactant is sodium lauryl sulfate.

BB. The dentifrice composition of paragraphs A-AA wherein the soluble fluoride ion source is selected from the group consisting of sodium fluoride, stannous fluoride, indium fluoride, sodium monofluorophosphate, and combinations thereof.

CC. The dentifrice composition of paragraphs A-BB comprising from about 20% to about 90% water; in another example 40% to about 70%; and in another example from about 50% to about 60%.

DD. The dentifrice composition of paragraphs A-BB comprising up to about 20% water; in another example up to about 15% water; in another example up to about 10% water; in another example up to about 8% water.

EE. A method of protecting against cavities, gingivitis, plaque, sensitivity, tartar, staining, and/or acid erosion by administering to a subject the composition of paragraphs A-DD and contacting the composition to the subject's tooth surfaces.

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   a. an abrasive comprising precipitated silica particles characterized by;
      (i) a BET surface area in a range from about 0.1 to about 9 $m^2/g$;
      (ii) a pack density in a range from about 35 to about 55 $lb/ft^3$;
      (iii) an Einlehner abrasion value in a range from about 8 to about 25 mg lost/100,000 revolutions;
      (iv) a total mercury intrusion pore volume in a range from about 0.4-1.2cc/g; and
      (v) a stannous compatibility in a range from about 70 to about 99%;
      (vi) wherein the abrasive comprises large pores of a size of approximately 1000 Angstroms or greater and lacks small pores sized less than approximately 500-1000 Angstroms;
   b. a stannous ion source wherein the extractable stannous ions after 30 days at 40° C. is greater than about 75% of the total stannous ion concentration.

2. The dentifrice composition of claim 1 wherein the composition has an average RDA of less than about 250.

3. The dentifrice composition of claim 1 wherein the extractable stannous ion concentration is greater than about 500 ppm.

4. The dentifrice composition of claim 1 wherein the extractable stannous ions after 30 days at 40° C. is greater than about 80% of the initial extractable stannous ion concentration.

5. The dentifrice composition of claim 1 wherein the composition has an average PCR from about 90 to about 150.

6. The dentifrice composition of claim 1 wherein the precipitated silica particles have a total mercury intrusion from about 0.75 to about 1.05.

7. A dentifrice composition comprising:
   a. an abrasive comprising precipitated silica particles characterized by;
      (i) a BET surface area in a range from about 0.1 to about 9 $m^2/g$;
      (ii) a pack density in a range from about 35 to about 55 $lb/ft^3$;
      (iii) an Einlehner abrasion value in a range from about 8 to about 25 mg lost/100,000 revolutions;
      (iv) a total mercury intrusion pore volume in a range from about 0.4-1.2 cc/g; and
      (v) a stannous compatibility in a range from about 70 to about 99%;
      (vi) wherein the abrasive comprises large pores of a size of approximately 1000 Angstroms or greater and lacks small pores sized less than approximately 500-1000 Angstroms;
   b. a stannous ion source wherein an extractable stannous ion concentration after 30 days at 40° C. is greater than about 75% of the total stannous ion concentration;
   c. a fluoride ion source wherein the percent soluble fluoride after 30 days at 40° C. is greater than about 75% of the initial fluoride concentration;
   wherein the average RDA is less than about 220.

8. The dentifrice composition of claim 7 wherein the extractable stannous ions after 30 days at 40° C. is greater than about 80% of the initial extractable stannous ion concentration.

9. The dentifrice composition of claim 7 wherein the extractable stannous ions after 30 days at 40° C. is greater than about 90% of the initial extractable stannous ion concentration.

10. A dentifrice composition comprising:
    a. an abrasive comprising precipitated silica characterized by;
       (i) a BET surface area in a range from about 0.1 to about 9 $m^2/g$;
       (ii) a pack density in a range from about 35 to about 55 $lb/ft^3$;
       (iii) an Einlehner abrasion value in a range from about 8 to about 25 mg lost/100,000 revolutions;
       (iv) a total mercury intrusion pore volume in a range from about 0.4-1.2cc/g; and
       (v) a stannous compatibility in a range from about 70 to about 99%;
       (vi) wherein the abrasive comprises large pores of a size of approximately 1000 Angstroms or greater and lacks small pores sized less than approximately 500-1000 Angstroms;
    b. a stannous ion source wherein the composition wherein an extractable stannous ions after 30 days at 40° C. is greater than about 80% of the initial extractable stannous ion concentration;
    c. a soluble fluoride ion source wherein the composition comprises from about 550 ppm to about 1100 ppm soluble fluoride ions;
    wherein the dentifrice composition has an average RDA less than about 250; wherein the dentifrice composition has an average PCR greater than about 90.

11. The dentifrice composition of claim 10 wherein the extractable stannous ions after 30 days at 40° C. is greater than about 85% of the initial extractable stannous ion concentration.

12. The dentifrice composition of claim 10 wherein the average RDA is less than about 220.

13. The dentifrice composition of claim 10 wherein the average RDA is less than about 200.

14. The dentifrice composition of claim 10 wherein the average PCR is greater than 110.

15. The dentifrice composition of claim 14 wherein the average PCR is greater than 120.

16. The dentifrice composition of claim 10 further comprising an antimicrobial agent selected from the group consisting of zinc citrate, zinc lactate, and combinations thereof, wherein the dentifrice composition comprises from about 900 ppm to 1750 ppm soluble zinc ions.

17. The dentifrice composition of claim 10 comprising from about 5% to about 30% abrasive.

18. The dentifrice composition of claim 10 wherein the precipitated silica particles have a total mercury intrusion from 0.9 to about 1.1 cc/g.

19. The dentifrice composition of claim 10 wherein the precipitated silica particles have a BET surface area in a range from about 0.1 to about 7 $m^2/g$.

* * * * *